United States Patent

De Manteuil et al.

Patent Number: 6,048,875
Date of Patent: Apr. 11, 2000

[54] BENZOTHIOPHENE, BENZOFURAN AND INDOLE COMPOUNDS

[75] Inventors: Guillaume De Manteuil, Suresnes; Christine Lila, Viroflay; Tony Verbeuren, Vernouillet; Alain Rupin, Savonnieres, all of France

[73] Assignee: Adir et Compagnie, Courbevoie, France

[21] Appl. No.: 09/299,271

[22] Filed: Apr. 26, 1999

[30] Foreign Application Priority Data

Apr. 27, 1998 [FR] France ................... 98 05239

[51] Int. Cl.[7] .................. A61K 31/44; A61K 31/47; A61K 31/38; C07D 409/06; C07D 409/14

[52] U.S. Cl. .................... 514/314; 514/333; 514/337; 514/443; 546/174; 546/256; 546/281.1; 549/54; 549/55

[58] Field of Search ................ 546/281.1, 174, 546/256; 514/337, 314, 333, 443; 549/54, 55

[56] References Cited

U.S. PATENT DOCUMENTS 4,663,344 5/1987 Durette ................... 514/443
5,356,926 10/1994 Boschelli ................ 514/445

*Primary Examiner*—Evelyn Mei Huang
*Attorney, Agent, or Firm*—The Firm of Gordon W. Hueschen

[57] ABSTRACT

A compound of formula (I):

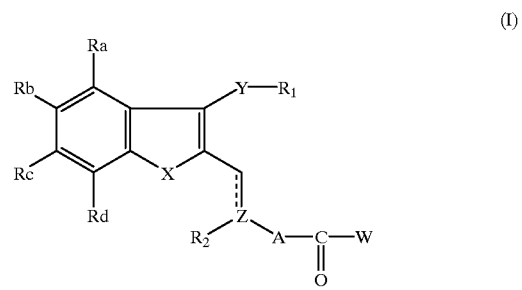

wherein:
- X represents oxygen, sulphur, or $NR_3$ wherein $R_3$ is as defined in the description,
- Y represents oxygen, sulphur, $NR_3$, or may a single bond when X represents $NR_3$,
- Z represents nitrogen, carbon, or CH,
- A represents a single bond, alkylene (optionally substituted), arylene, cycloalkylene, heterocycle, or $-SO_2-R_4-$ wherein $R_4$ is as defined in the description,
- W represents hydroxy, alkoxy, aryloxy, arylalkoxy, cycloalkyloxy, heterocycle bonded to oxygen, amino, or hydroxyamino,
- Ra, Rb, Rc, Rd, which may be the same or different, each independently of the others are as defined in the description,
- $R_1$ represents aryl substituted by one to five identical or different substituents, each independently of the others,
- $R_2$ represents hydrogen, alkyl, aryl, arylalkyl, cycloalkyl, heterocycle, heterocycloalkyl, or another group as defined in the description, isomers and addition salts thereof with a pharmaceutically-acceptable acid or base, and medicinal products containing the same which are useful in the treatment of thrombosis, pathologies for which the origin is thrombosis, or pathologies causing an increase in risk of thrombosis.

20 Claims, No Drawings

BENZOTHIOPHENE, BENZOFURAN AND INDOLE COMPOUNDS

FIELD OF THE INVENTION

The present invention relates to new benzothiophene, benzofuran and indole compounds. Those new compounds are useful for their therapeutic activity in the field of fibrinolysis and thrombosis, by virtue of their property of inhibiting the activity of PAI-1.

PAI-1 is a powerful inhibitor of plasminogen activators (tissue plasminogen activator and urokinase). In vitro and in vivo it causes inhibition of the breakdown of the fibrinous clots formed by the action of thrombin on fibrinogen. A number of epidemiological studies have shown that, in man, high levels of PAI-1 are associated with more frequent occurrence of thromboembolic disorders. Moreover, in experimental models of thrombosis and thrombolysis, inhibition of the activity of PAI-1 by anti-PAI-1 monoclonal antibodies reduces the incidence of thromboses or reocclusions. The therapeutic value of molecules having the property of inhibiting the activity of PAI-1 in the fibrinous clot that has been formed or that is in the process of being formed is thus to enable it to be broken down at an early stage before it is complexed with Factor XIIIa and thus to reduce the incidence of thromboembolic accidents in patients having high levels of PAI-1. Such compounds are therapeutically valuable in all pathologies for which the origin is thrombosis (such as myocardial infarction, angina, intermittent claudication, cerebral vascular accidents, deep vein thrombosis or pulmonary embolism) and in pathologies in which risk of thrombosis is increased (such as hypertension, hypercholesterolaemia, diabetes, obesity, genetic coagulation anomalies (Factor V Leiden, deficit in proteins C and S) or acquired coagulation anomalies).

The compounds of the present invention, in addition to being new, have proved to be more powerful PAI-1 inhibitors than those described in the literature, which thus makes them potentially useful in the treatment of thrombosis, or of pathologies for which the origin is thrombosis.

A number of antithrombotics have been described in the literature. This is the case, more especially, of the compounds described in Patent Specifications WO 97/45424, WO 94/08962, EP 540 051 and GB 2225012.

DETAILED DESCRIPTION OF THE INVENTION

More especially, the present invention relates to compounds of formula (I):

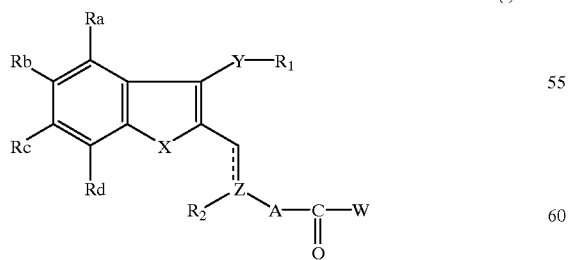

wherein:

X represents an oxygen atom, a sulphur atom, or an $NR_3$ group wherein $R_3$ represents a hydrogen atom, a linear or branched ($C_1$–$C_6$)alkyl group, a linear or branched ($C_1$–$C_6$)acyl group, an aryl group, an aryl-($C_1$–$C_6$)alkyl group in which the alkyl moiety is linear or branched, or a heteroaryl-($C_1$–$C_6$)alkyl group in which the alkyl moiety is linear or branched, Y represents an oxygen atom, a sulphur atom, an $NR_3$ group, (the $R_3$ group being as defined above), or may represent a single bond when X represents an $NR'_3$ group wherein $R'_3$ represents a heteroaryl-($C_1$–$C_6$)alkyl group in which the alkyl moiety is linear or branched, Z represents a nitrogen atom when the bond that links it to the adjacent carbon atom is single (—), a carbon atom or a CH group depending on whether the bond that links it to the adjacent carbon atom is single (—) or double (=), A represents a single bond, a ($C_1$–$C_6$)alkylene group (optionally substituted by one or more linear or branched ($C_1$–$C_6$)alkyl groups, aryl groups, aryl-($C_1$–$C_6$)alkyl groups in which the alkyl moiety is linear or branched, cycloalkyl groups, or by heterocycle groups), an arylene group, a cycloalkylene group, a heterocycle, or an —$SO_2$—$R_4$— group (the $SO_2$ moiety being linked to Z) wherein $R_4$ represents a linear or branched ($C_1$–$C_6$)alkylene group, an arylene group, an aryl-($C_1$–$C_6$)alkylene group in which the alkylene moiety is linear or branched, a cycloalkylene group or a heterocycle, W represents a hydroxy group, a linear or branched ($C_1$–$C_6$)alkoxy group, an aryloxy group, an aryl-($C_1$–$C_6$)alkoxy group in which the alkoxy moiety is linear or branched, a cycloalkyloxy group, a heterocycle bonded to an oxygen atom, an amino group (which may itself be substituted by one or two identical or different groups, each independently of the other selected from linear or branched ($C_1$–$C_6$)alkyl, aryl, aryl-($C_1$–$C_6$)alkyl in which the alkyl moiety is linear or branched, and cycloalkyl), or a hydroxyamino group, Ra, Rb, Rc, Rd, which may be identical or different, each independently of the others represent a hydrogen atom, a halogen atom, a hydroxy group, a cyano group, a nitro group, a linear or branched ($C_1$–$C_6$)alkyl group, a linear or branched ($C_1$–$C_6$)alkoxy group, a linear or branched ($C_1$–$C_6$)acyl group, a carboxy group, a linear or branched ($C_1$–$C_6$)alkoxy-carbonyl group, a linear or branched ($C_1$–$C_6$)trihaloalkyl group, an amino group (optionally substituted by one or two identical or different groups, each independently of the other selected from linear or branched ($C_1$–$C_6$)alkyl, aryl and aryl-($C_1$–$C_6$)alkyl in which the alkyl moiety is linear or branched), an aryloxy group, an aryl-($C_1$–$C_6$)alkoxy group in which the alkoxy moiety is linear or branched, a heteroaryloxy group, or a heteroaryl-($C_1$–$C_6$)alkoxy group in which the alkoxy moiety is linear or branched, or Ra+Rb, Rb+Rc or Rc+Rd represents a group of formula -$U_1$-V-$U_2$ (in which case each of the remaining group Ra, Rb, Rc, Rd takes one of the definitions given above), wherein:

$U_1$ and $U_2$, which may be identical or different, represent an oxygen atom, a sulphur atom, or an NH or $CH_2$ group, V represents a linear ($C_1$–$C_4$)alkylene group, optionally substituted by one or more linear or branched ($C_1$–$C_6$)alkyl groups, aryl groups, aryl-($C_1$–$C_6$)alkyl groups in which the alkyl moiety is linear or branched, heteroaryl groups, or by heteroaryl-($C_1$–$C_6$)alkyl groups in which the alkyl moiety is linear or branched, or V represents a group of formula

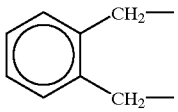

with the proviso that Ra, Rb, Rc and Rd cannot simultaneously represent a hydrogen atom, $R_1$ represents:

an aryl group substituted by from one to five identical or different substituents, each independently of the others selected from halogen, hydroxy, cyano, nitro, carboxy, linear or branched $(C_1-C_6)$alkyl, linear or branched $(C_1-C_6)$alkoxy, linear or branched $(C_1-C_6)$ acyl, linear or branched $(C_1-C_6)$alkoxy-carbonyl, trihalo-$(C_1-C_6)$alkyl (in which the alkyl moiety is linear or branched and is optionally substituted by a hydroxy group), trihalo-$(C_1-C_6)$-alkoxy in which the alkoxy moiety is linear or branched, amino (optionally substituted by one or two linear or branched $(C_1-C_6)$alkyl groups, one of which alkyl groups may be optionally substituted by an amino group, by a linear or branched $(C_1-C_6)$alkylamino group, or by a di-$(C_1-C_6)$alkylamino group in which the alkyl moieties are each linear or branched), amino-$(C_1-C_6)$alkoxy in which the alkoxy moiety is linear or branched (the amino moiety of which may be substituted by one or two, identical or different, linear or branched $(C_1-C_6)$alkyl groups), $(C_1-C_6)$ alkoxycarbonyl-$(C_1-C_6)$alkyl in which the alkoxy and alkyl moieties are each linear or branched, linear or branched $(C_1-C_6)$-alkylcarbonylamino, aryl-$(C_1-C_6)$alkyl in which the alkyl moiety is linear or branched, aryloxy, aryl-$(C_1-C_6)$alkoxy in which the alkoxy moiety is linear or branched, arylamino, aryl-$(C_1-C_6)$alkylamino in which the alkyl moiety is linear or branched, arylsulphanyl, aryl-$(C_1-C_6)$ alkylsulphanyl in which the alkyl moiety is linear or branched, heteroaryl, heteroaryl-$(C_1-C_6)$alkyl in which the alkyl moiety is linear or branched, heteroaryloxy, heteroaryl-$(C_1-C_6)$alkoxy in which the alkoxy moiety is linear or branched, heteroarylamino, heteroaryl-$(C_1-C_6)$alkylamino in which the alkyl moiety is linear or branched, heteroarylsulphanyl and heteroaryl-$(C_1-C_6)$ alkylsulphanyl in which the alkyl moiety is linear or branched, an aryl group of formula

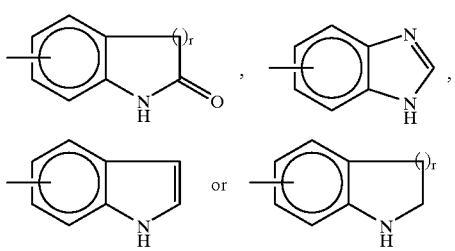

wherein r is an integer 1 or 2, a 1-hydroxy-2(1H)-pyridinone group, or an optionally substituted heteroaryl group, $R_2$ represents a hydrogen atom, a linear or branched $(C_1-C_6)$alkyl group, an aryl group, an aryl-$(C_1-C_6)$ alkyl group in which the alkyl moiety is linear or branched, a cycloalkyl group, an optionally substituted heterocycle or a heterocycle bonded to a linear or branched $(C_1-C_6)$-alkyl group, their isomers and addition salts thereof with a pharmaceutically acceptable acid or base.

Among the pharmaceutically acceptable acids there may be mentioned by way of non-limiting example hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid, etc.

Among the pharmaceutically acceptable bases there may be mentioned by way of non-limiting example sodium hydroxide, potassium hydroxide, triethylamine, tert-butylamine, etc.

Aryl group is understood to be a phenyl, naphthyl, tetrahydronaphthyl or dihydronaphthyl group, each of those groups being optionally substituted by one or more identical or different substituents selected from halogen atoms, hydroxy, cyano, nitro, linear or branched $(C_1-C_6)$-alkyl, linear or branched $(C_1-C_6)$trihaloalkyl, linear or branched $(C_1-C_6)$alkoxy, linear or branched $(C_1-C_6)$acyl, carboxy, linear or branched $(C_1-C_6)$alkoxycarbonyl and amino groups (amino optionally being substituted by one or two identical or different linear or branched $(C_1-C_6)$alkyl groups).

Cycloalkyl group is understood to be a mono- or bi-cyclic group, containing from 3 to 8 carbon atoms.

Heterocycle is understood to be a mono- or bi-cyclic, saturated or unsaturated, aromatic or non-aromatic, group having from 5 to 12 ring members, containing one, two or three identical or different hetero atoms selected from oxygen, nitrogen and sulphur, it being understood that the heterocycle may be optionally substituted by one or more identical or different substituents selected from halogen atoms, hydroxy, linear or branched $(C_1-C_6)$alkyl, linear or branched $(C_1-C_6)$trihaloalkyl, linear or branched $(C_1-C_6)$ alkoxy, aryloxy, aryl$(C_1-C_6)$alkoxy in which alkoxy moiety is linear or branched, amino (amino optionally being substituted by one or two linear or branched $(C_1-C_6)$alkyl groups), linear or branched $(C_1-C_6)$acyl, linear or branched $(C_1-C_6)$alkoxycarbonyl, nitro and oxo groups.

More particularly, heteroaryl is understood to be an unsaturated mono- or bi-cyclic heterocycle optionally substituted, at least one of the rings of which is aromatic. There may be mentioned by way of non-limiting example heteroaryls such as pyridine, pyrimidine, quinoline, isoquinoline, 1,3-dihydro-2H-pyrrolopyridin-2-one, 3H-imidazopyridine, 1H-pyrrolopyridine, 1,2,3,4-tetrahydronaphthpyridine or 2,3-dihydro-1H-pyrrolopyridine.

Preferred compounds of the invention are those wherein X represents a sulphur atom or an $NR_3$ group wherein $R_3$ is as defined for formula (I).

Preferred compounds of the invention are those wherein Y represents an oxygen atom.

The $R_1$ substituents preferred according to the invention are groups selected from phenyl optionally substituted by one group as defined for formula (I), optionally substituted quinolyl and optionally substituted pyridinyl.

The $R_2$ substituents preferred according to the invention are the groups selected from aryl and heterocycle, each of those groups being optionally substituted. According to an advantageous embodiment, the preferred $R_2$ substituent is the pyridinyl group.

According to an advantageous embodiment of the invention, preferred compounds are those wherein X represents a sulphur atom and Y represents an oxygen atom.

According to another especially advantageous embodiment of the invention, the preferred compounds are those wherein:

X represents a sulphur atom,

Y represents an oxygen atom, $R_1$ represents an optionally substituted phenyl group or an optionally substituted pyridinyl group, A represents a single bond when Z represents a carbon atom or a CH group.

According to a third advantageous embodiment, the preferred compounds of the invention are those wherein:

X represents a sulphur atom,

Y represents an oxygen atom, $R_1$ represents a phenyl group optionally substituted by one group as defined for formula (I), A represents an alkylene group (optionally substituted by a linear or branched ($C_1$–$C_6$)alkyl group, an aryl group, an aryl-($C_1$–$C_6$)alkyl group in which the alkyl moiety is linear or branched) or an arylene group, when Z represents a nitrogen atom.

The preferred compounds according to the invention are:
(E)-3-[5,6-dimethoxy-3-(4-methoxyphenoxy)benzo[b]thiophen-2-yl]-2-(4-pyridinyl)-2-propenoic acid,
(E)-3-[5,6-bis(benzyloxy)-3-(4-methoxyphenoxy)benzo[b]thiophen-2-yl]-2-(4-pyridinyl)-2-propenoic acid,
(E)-3-[5,6-bis(benzyloxy)-3-(4-benzyloxyphenoxy)benzo[b]thiophen-2-yl]-2-(4-pyridyl)-2-propenoic acid,
(E)-3-[5,6-bis(benzyloxy)-3-(3-pyridinyloxy)benzo[b]thiophen-2-yl]-2-(4-pyridinyl)-2-propenoic acid,
(E)-3-[5,6-bis(benzyloxy)-3-(4-hydroxyphenoxy)benzo[b]thiophen-2-yl]-2-(4-pyridinyl)-2-propenoic acid,
(E)-3-{5,6-bis(benzyloxy)-3-[(6-methyl-3-pyridinyl)oxy]benzo[b]thiophen-2-yl}-2-(4-pyridinyl)-2-propenoic acid,
(E)-3-{5-(benzyloxy)-3-[4-(benzyloxy)phenoxy]-6-methoxy-benzo[b]thiophen-2-yl}-2-(4-pyridinyl)-2-propenoic acid,
(E)-3-[5,6-bis(benzyloxy)-3-(6-quinolinyloxy)benzo[b]thiophen-2-yl]-2-(4-pyridinyl)-2-propenoic acid,
(E)-3-{5,6-bis(benzyloxy)-3-[(6-methoxy-3-pyridinyl)oxy]-benzo[b]thiophen-2-yl}-2-(4-pyridinyl)-2-propenoic acid,
(E)-3-{5,6-bis(benzyloxy)-3-[4-(4-pyridinyl)phenoxy] benzo [b]thiophen-2-yl }-2-(4-pyridinyl)-2-propenoic acid, and
(E)-3-[5-benzyloxy-6-methoxy-3-(3-pyridinyl)oxy-benzo[b]thiophen-2-yl]-2-(4-pyridinyl)-2-propenoic acid.

The isomers, and addition salts with a pharmaceutically acceptable acid or base, of the preferred compounds of the invention are an integral part of the invention.

The invention relates also to a process for the preparation of the compounds of formula (I), characterised in that there is used as starting material a compound of formula (II):

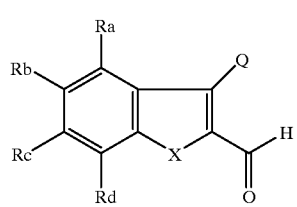

(II)

wherein Ra, Rb, Rc, Rd and X are as defined for formula (I) and Q represents a halogen atom or a hydroxy group and, preferably, Q represents a halogen atom when X represents a sulphur atom or an $NR_3$ group wherein $R_3$ is as defined for formula (I) and Q represents a hydroxy group when X represents an oxygen atom, which compound of formula (II) is reacted, under basic conditions, either when Q represents a halogen atom:
with a compound of formula (III),

(III)

wherein $R_1$ is as defined for formula (I) and $Y_1$ represents an oxygen atom, a sulphur atom or an $NR_3$ group wherein $R_3$ is as defined for formula (I), to yield the compounds of formula (IV/a):

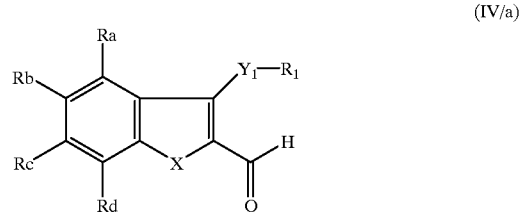

(IV/a)

wherein Ra, Rb, Rc, Rd, $R_1$, X and $Y_1$ are as defined hereinabove, or with a compound of formula (V):

(V)

wherein $R_1$ is as defined for formula (I), to yield the compounds of formula (IV/b):

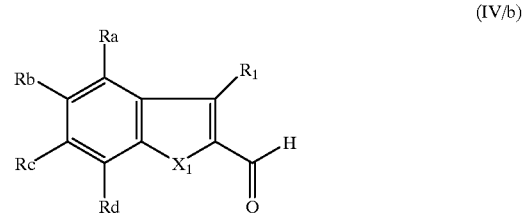

(IV/b)

wherein Ra, Rb, Rc, Rd and $R_1$ are as defined hereinabove and $X_1$ represents an $NR_3$ group wherein $R_3$ represents a heteroaryl-($C_1$–$C_6$)alkyl group in which the alkyl moiety is linear or branched, or when Q represents a hydroxy group, with a compound of formula (VI),

(VI)

wherein Hal represents a halogen atom and $R_1$ is as defined hereinabove, to yield the compounds of formula (IV/c):

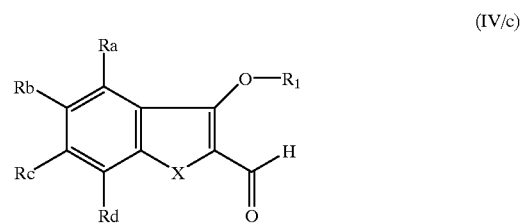

(IV/c)

wherein Ra, Rb, Rc, Rd, X and $R_1$ are as defined hereinabove, the totality of the compounds of formulae (IV/a), (IV/b) and (IV/c) constituting the compounds of formula (IV):

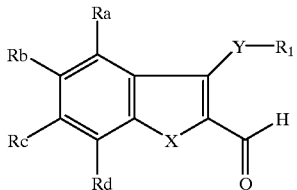

(IV)

wherein Ra, Rb, Rc, Rd, $R_1$, X and Y are as defined for formula (I), which compounds of formula (IV):
are condensed, in the presence of acetic anhydride, with a compound of formula (VII),

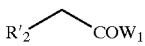

(VII)

wherein $R'_2$ has the same definition as $R_2$ for formula (I), with the exception that $R'_2$ cannot represent a hydrogen atom, and $W_1$ represents a linear or branched ($C_1$–$C_6$)alkoxy group, an aryloxy group, an aryl-($C_1$–$C_6$)alkoxy group in which the alkoxy moiety is linear or branched, a cycloalkyloxy group, a heterocycle bonded to an oxygen atom, or an amino group (which may itself be substituted by one or two identical or different groups, each independently of the other selected from linear or branched ($C_1$–$C_6$)alkyl, aryl, aryl-($C_1$–$C_6$)-alkyl in which the alkyl moiety is linear or branched, and cycloalkyl), to yield the compounds of formula (I/a), a particular case of the compounds of formula (I):

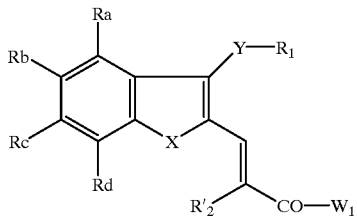

(I/a)

wherein Ra, Rb, Rc, Rd, $R_1$, $R'_2$, X, Y and $W_1$ are as defined hereinabove, which compounds of formula (I/a) are, if desired, subjected to:
  either to conditions of catalytic hydrogenation, in the presence of palladium, to yield the compounds of formula (I/b), a particular case of the compounds of formula (I):

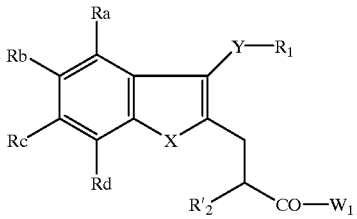

(I/b)

wherein Ra, Rb, Rc, Rd, $R_1$, $R'_2$, X, Y and $W_1$ are as defined hereinabove, or to conditions of hydrolysis, in a basic medium, to yield the compounds of formula (I/c), a particular case of the compounds of formula (I):

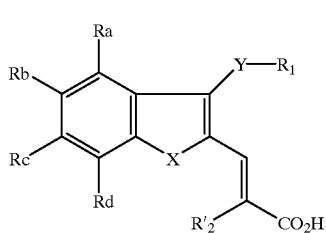

(I/c)

wherein Ra, Rb, Rc, Rd, $R_1$, $R'_2$, X and Y are as defined hereinabove,
  the double bond of which compounds of formula (I/c) is, if desired, reduced by catalytic hydrogenation, to yield the compounds of formula (I/d), a particular case of the compounds of formula (I):

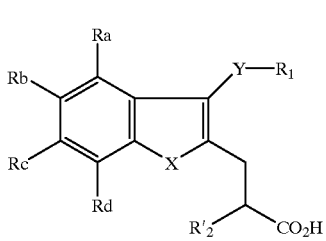

(I/d)

wherein Ra, Rb, Rc, Rd, $R_1$, $R'_2$, X and Y are as defined hereinabove,
  or are subjected to the action of a phosphorus ylid of formula (VIII),

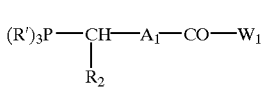

(VIII)

wherein R' represents a linear or branched ($C_1$–$C_6$)alkyl group, or a phenyl group, $R_2$ is as defined for formula (I), $W_1$ is as defined hereinabove and $A_1$ represents a single bond, an alkylene group (optionally substituted by one or more linear or branched ($C_1$–$C_6$)alkyl groups, aryl groups, aryl-($C_1$–$C_6$) alkyl groups in which the alkyl moiety is linear or branched, cycloalkyl groups, or by a heterocycle groups), an arylene group, a cycloalkylene group or a heterocycle, to yield the compounds of formula (I/e), a particular case of the compounds of formula (I):

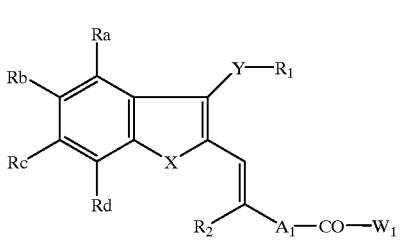

(I/e)

wherein Ra, Rb, Rc, Rd, $R_1$, $R_2$, X, Y, $A_1$ and $W_1$ are as defined hereinabove, which compounds of formula (I/e) are, if desired, subjected to:

either to conditions of hydrolysis, under basic conditions, to yield the compounds of formula (I/f), a particular case of the compounds of formula (I):

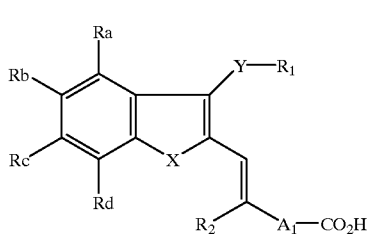
(I/f)

wherein Ra, Rb, Rc, Rd, $R_1$, $R_2$, X, Y and $A_1$ are as defined hereinabove, or to conditions of catalytic hydrogenation, to yield the compounds of formula (I/g), a particular case of the compounds of formula (I):

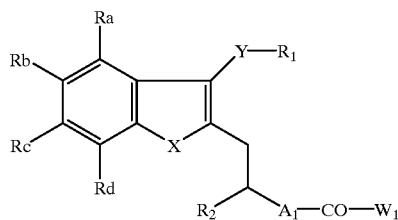
(I/g)

wherein Ra, Rb, Rc, Rd, $R_1$, $R_2$, X, Y, $A_1$ and $W_1$ are as defined hereinabove, which compounds of formula (I/g) may be treated under conditions of basic hydrolysis, to yield the compounds of formula (I/h), a particular case of the compounds of formula (I):

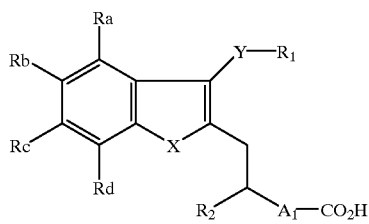
(I/h)

wherein Ra, Rb, Rc, Rd, $R_1$, $R_2$, X, Y and $A_1$ are as defined hereinabove, or the aldehyde function of which compounds of formula (IV) is reduced to the primary alcohol, to yield the compounds of formula (IX):

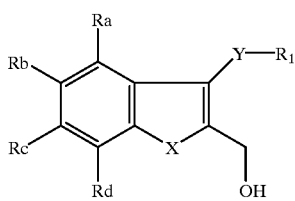
(IX)

wherein Ra, Rb, Rc, Rd, $R_1$, X and Y are as defined for formula (I), the terminal hydroxy of which compounds of formula (IX) is replaced by a halogen atom, according to conventional conditions, to yield the compounds of formula (X):

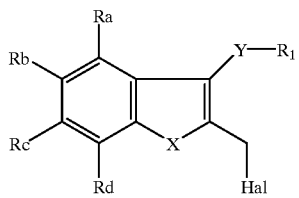
(X)

wherein Ra, Rb, Rc, Rd, $R_1$, X and Y are as defined hereinabove, and Hal represents a chlorine or bromine atom, in which compounds of formula (X):

the halogen atom is replaced, under basic conditions, by an aminated compound of formula (XI):

$R_2$-NH-$A_1$-CO-$W_1$ (XI)

wherein $R_2$ is as defined for formula (I) and $A_1$ and $W_1$ are as defined hereinabove, to yield the compounds of formula (I/i), a particular case of the compounds of formula (I):

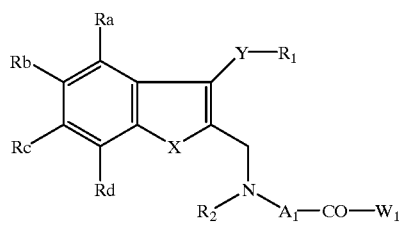
(I/i)

wherein Ra, Rb, Rc, Rd, $R_1$, $R_2$, X, Y, $A_1$ and $W_1$ are as defined hereinabove, the terminal carbonyl group of which compounds of formula (I/i) may be hydrolysed under basic conditions to yield the compounds of formula (I/j), a particular case of the compounds of formula (I):

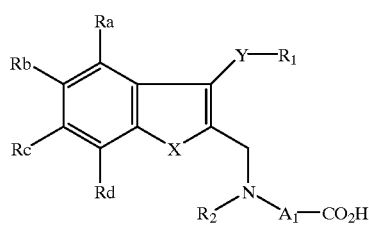
(I/j)

wherein Ra, Rb, Rc, Rd, $R_1$, $R_2$, X, Y and $A_1$ are as defined hereinabove, or which compounds of formula (X) are initially treated with sodium azide, the resulting azide being reduced to the primary amine under conditions of catalytic hydrogenation, to yield the compounds of formula (XII):

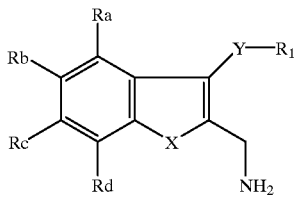

(XII)

wherein Ra, Rb, Rc, Rd, $R_1$, X and Y are as defined for formula (I), which compounds of formula (XII) are condensed, under basic conditions, with a chlorosulphonyl compound of formula (XIII):

Cl-SO$_2$-R$_4$-CO-W$_1$      (XIII)

wherein $R_4$ is as defined for formula (I), and $W_1$ is as defined hereinabove, to yield the compounds of formula (I/k), a particular case of the compounds of formula (I),

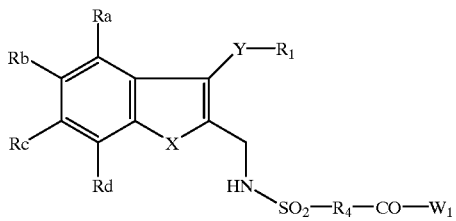

(I/k)

wherein Ra, Rb, Rc, Rd, $R_1$, $R_4$, X, Y and $W_1$ are as defined hereinabove, which compounds of formula (I/k):

are subjected, if desired, to conditions of hydrolysis under basic conditions, to yield the compounds of formula (I/l), a particular case of the compounds of formula (I):

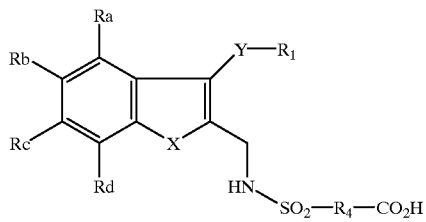

(I/l)

wherein Ra, Rb, Rc, Rd, $R_1$, $R_4$, X and Y are as defined hereinabove, or condensed, in a basic medium, with a compound of formula (XIV):

Hal-R'$_2$      (XIV)

wherein Hal represents a halogen atom, such as iodine, and R'$_2$ is as defined hereinabove, to yield the compounds of formula (I/m), a particular case of the compounds of formula (I):

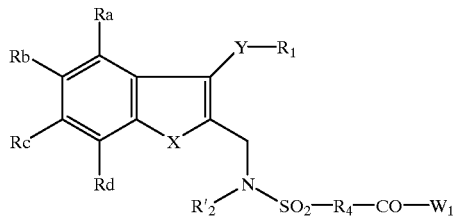

(I/m)

wherein Ra, Rb, Rc, Rd, $R_1$, R'$_2$, $R_4$, X, Y and $W_1$ are as defined hereinabove, which compounds of formula (I/m) may be treated by conditions of hydrolysis in a basic medium, to yield the compounds of formula (I/n), a particular case of the compounds of formula (I):

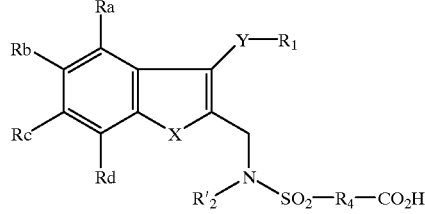

(I/n)

wherein Ra, Rb, Rc, Rd, $R_1$, R'$_2$, $R_4$, X and Y are as defined hereinabove, the totality of the compounds of formulae (I/c), (I/d), (I/f), (I/h), (I/j), (I/l) and (I/n) constituting the compounds of formula (I'):

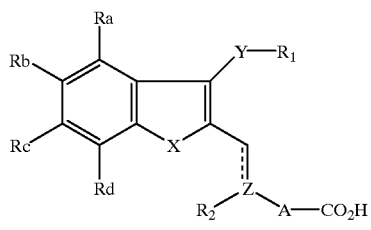

(I')

wherein Ra, Rb, Rc, Rd, $R_1$, $R_2$, X, Y, Z and A are as defined for formula (I), which compounds of formula (I') are reacted with an O-substituted hydroxylamine, to yield, after deprotection of the hydroxylamine function, the compounds of formula (I/o), a particular case of the compounds of formula (I):

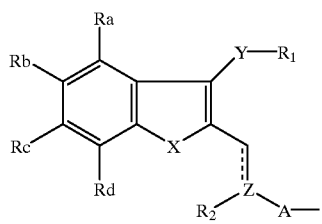

(I/o)

wherein Ra, Rb, Rc, Rd, $R_1$, $R_2$, X, Y, Z and A are as defined hereinabove, the compounds (I/a) to (I/o) constituting the totality of the compounds of the invention, which are purified, if necessary, according to a conventional purification technique, which may be separated, if desired, into their different isomers according to a conventional separation technique, and which are converted, where appropriate, into addition salts thereof with a pharmaceutically acceptable acid or base.

The compounds of formula (II) are obtained according to conventional methods of organic synthesis. For example, the compounds of formula (II) wherein X represents an oxygen atom and Q represents a hydroxy group, are obtained starting from compounds of formula (II/A):

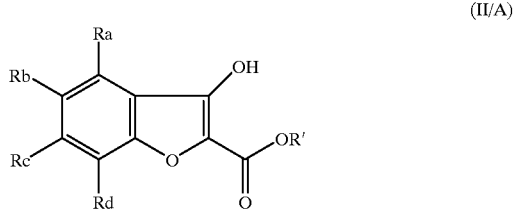

the synthesis scheme of which is described in *J. Med. Chem.*, 1992, 35, 958–965, and wherein Ra, Rb, Rc, Rd are as defined for formula (I) and R' represents a linear or branched $(C_1-C_6)$alkyl group, the hydroxy function of which is protected, under basic conditions, by a trialkylsilyl group, and the ester function of which is then reduced, by the action of $LiAlH_4$ for example, to the primary alcohol function, the latter then being oxidised to the aldehyde function, the alcohol function thereof then being deprotected under the action of n-$Bu_4NF$, enabling the particular compounds of formula (II) wherein X represents an oxygen atom and Q represents a hydroxy group to be obtained.

The particular compounds of formula (II) wherein X represents an $NR_3$ group are obtained starting from compounds of formula (II/B):

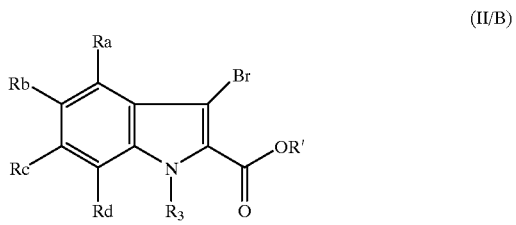

the synthesis scheme of which is described in *Heterocycles*, 1992, 34 (12), 2349–62 and in *Synthesis*, 1984, 862–865, and wherein Ra, Rb, Rc, Rd, $R_3$ are as defined for formula (I) and R' represents a linear or branched $(C_1-C_6)$alkyl group, the ester function of which is reduced to the primary alcohol function, the latter then being oxidised under the action of manganese dioxide to the aldehyde function, to yield the compounds of formula (II) wherein X represents an $NR_3$ group and Q represents a halogen atom.

The particular compounds of formula (II) wherein X represents a sulphur atom are obtained starting from compounds of formula (II/C):

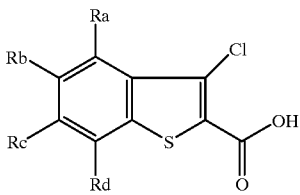

the synthesis scheme of which is described in *J. Heterocyclic. Chem.*, 1971, 8, 711–714, and wherein Ra, Rb, Rc and Rd are as defined hereinabove, the carboxylic acid function of which is first reduced to the primary alcohol and then oxidised to the aldehyde to yield the compounds of formula (II) wherein X represents a sulphur atom and Q represents a halogen atom.

The compounds of formulae (III), (IV), (VII), (VIII), (XI), (XIII) and (XIV) are either commercial products or are obtained according to conventional methods of organic synthesis.

The present invention relates also to pharmaceutical compositions comprising as active ingredient at least one compound of formula (I), its optical isomers or an addition salt thereof with a pharmaceutically acceptable base or acid, on its own or in combination with one or more inert non-toxic, pharmaceutically acceptable, excipients or carriers.

Among the pharmaceutical compositions according to the invention there may be mentioned more especially those that are suitable for oral, parenteral (intravenous, intramuscular or sub-cutaneous), per- or trans-cutaneous, nasal, rectal, perlingual, ocular or respiratory administration, and especially tablets or dragées, sublingual tablets, sachets gelatin capsules, lozenges, suppositories, creams, ointments, dermal gels, injectable or drinkable preparations, aerosols, eye or nose drops, etc.

The useful dosage varies according to the age and weight of the patient, the route of administration, the nature and severity of the disorder and whether any other associated treatments are being taken, and ranges from 0.1 mg to 1 g in one or more administrations per day.

The following Examples illustrate the invention but do not limit it in any way.

The starting materials used are known products or are prepared according to known procedures.

The different synthesis steps yield synthesis intermediates, for use in the preparation of the compounds of the invention.

The structures of the compounds described in the Examples and in the synthesis steps were determined according to the usual spectrophotometric techniques (infrared, NMR, mass spectrometry, etc.).

EXAMPLE 1

Ethyl (E)-3-[5,6dimethoxy-3-(4-methoxyphenoxy) benzo[b]thiophen-2-yl]-2-(4-pyridinyl)-2-propenoate
Step A: 3-Chloro-5,6-dimethoxy-benzo[b]thiophene-2-carbonyl chloride 0.025 mol of pyridine and, dropwise, 1.27 mol of $SOCl_2$ are added in succession at room temperature to a suspension of 0.25 ml of 3,4-dimethoxycinnamic acid in 350 ml of chlorobenzene. The reaction mixture is then refluxed for 2 days. After returning to room temperature, a precipitate forms. Filtration, rinsing with hexane and drying yield 53.7 g of the expected product.
Melting point: 202° C.

Step B: 3-Chloro-5,6-dimethoxy-benzo[b]thiophene-2-carboxylic acid 40 ml of water are added to a solution of 70 mmol of the compound of Step A in 250 ml of dioxane. After 20 hours' reflux and then return to room temperature, a precipitate forms. After filtration and rinsing with water until neutral, the precipitate is dried over $P_2O_5$ under reduced pressure. 18.6 g of the expected product are thus isolated.

Melting point: >260° C.

Step C: (3-Chloro-5,6-dimethoxy-benzo[b]thiophen-2-yl) methanol

A suspension of 68 mmol of the compound obtained in Step B in 150 ml of tetrahydrofuran is added at 5° C. under an inert atmosphere to a solution of 0.1 mol of $LiAlH_4$ in 60 ml of tetrahydrofuran. After 4 hours' reaction at room temperature, the reaction mixture is hydrolysed by the addition of water and then by an aqueous 2N sodium hydroxide solution. After 12 hours at room temperature, the reaction mixture is filtered over Celite. The organic phase is then concentrated under reduced pressure, taken up in dichloromethane and washed with water and then with a saturated NaCl solution. After the organic phase has been dried over calcium sulphate, the solution is concentrated under reduced pressure, enabling 15.7 g of the expected product to be obtained.

Melting point: 164° C.

Step D: 3-Chloro-5,6-dimethoxy-benzo[b]thiophene-2-carbaldehyde 96 mmol (1.6 equivalents) of $MnO_2$ are added at room temperature under an inert atmosphere to a suspension of 60.4 mmol of the compound obtained in Step C in 360 ml of toluene. After 6 hours' reaction at 80° C., 0.6 equivalent of $MnO_2$ is added to the reaction mixture, followed six hours later by 0.6 equivalent of $MnO_2$. The reaction mixture is then filtered while hot over Celite and rinsed with toluene. After 12 hours at room temperature, the filtrate precipitates. Filtration of the precipitate followed by rinsing with toluene and then with pentane enables 8.65 g of the expected product to be isolated.

Melting point: 280° C.

Step E: 5,6-Dimethoxy-3-(4-methoxyphenoxy)benzo[b] thiophene-2-carbaldehyde 1.1 equivalents of sodium hydride and then 0.033 mol of the product obtained in Step D are added at room temperature and under an inert atmosphere to a solution of 0.036 mol of 4-methoxyphenol in 250 ml of dimethylformamide. After 12 hours' reaction, the reaction mixture is concentrated under reduced pressure. The residue is then diluted in ethyl acetate, washed with water and then with an aqueous NaCl solution, dried over calcium sulphate, filtered and concentrated under reduced pressure. Chromatography over silica gel (dichloromethane/ethyl acetate: 98/2) enables 8.6 g of the expected product to be isolated.

Melting point: 138° C.

Step F: Ethyl (E)-3-[5,6-dimethoxy-3-(4-methoxyphenoxy) benzo[b]thiophen-2-yl]-2-(4-pyridinyl)-2-propenoate A solution containing 6 mmol of the product obtained in Step E, 30 mmol of ethyl 4-pyridylacetate and 5 ml of acetic anhydride is maintained at 100° C. for 18 hours. After returning to room temperature, the reaction mixture is hydrolysed by a saturated $NaHCO_3$ solution and extracted with ethyl acetate. The organic phases are then washed with water and then with an NaCl solution, dried over calcium sulphate, filtered and concentrated under reduced pressure. Chromatography over silica gel (dichloromethane/ethanol: 98/2) enables the expected product to be isolated.

Melting point: 164° C.

EXAMPLE 2

(E)-3-[5,6Dimethoxy-3-(4-methoxyphenoxy)benzo [b]thiophen-2-yl]-2-(4-pyridinyl)-2-propenoic acid A solution containing 3 mmol of the product of Example 1, 6 ml of an aqueous 1N sodium hydroxide solution and 20 ml of ethanol is refluxed for 2 hours. After returning to room temperature, the reaction mixture is concentrated under reduced pressure and the residue is then diluted in water and subsequently taken up in diethyl ether. The organic phase is then rendered acidic by the addition of 6 ml of a 1N HCl solution. A precipitate forms, which is filtered, rinsed with water and then dried under reduced pressure, enabling 1.3 g of the expected compound to be obtained.

Melting point: 208° C.

EXAMPLE 3

Sodium (E)-3-[5,6-dimethoxy-3-(4-methoxyphenoxy)benzo[b]thiophen-2-yl]-2-(4-pyridinyl)-2-propenoate Water is added to a suspension of 1.16 g of the product of Example 2 in 2.5 ml of 1N sodium hydroxide solution until completely diluted. Lyophilisation enables 1.22 g of the expected product to be isolated.

IR: 1630–1575 $cm^{-1}$ ($v_s$(C=O); $v_s$(C=C); $v_s$(C=N))

EXAMPLE 4

Sodium (E)-3-{3-[4-(benzyloxy)phenoxy]-5,6-dimethoxy-benzo[b]thiophen-2-yl}-2-(4-pyridinyl)-2-propenoate The procedure is as for Example 1 using 4-benzyloxyphenol as reagent in Step E, and then as for Examples 2 and 3.

Mass spectrum: FAB: $[M+H]^+$: m/z=562; $[M+Na]^+$: m/z=584

EXAMPLE 5

Sodium (E)-3-{5,6-dimethoxy-3-[(6-methoxy-2-naphthyl)-oxy]benzo[b]-thiophen-2-yl }-2-(4-pyridinyl)-2-propenoate The procedure is as for Example 4 using 6-methoxy-2-naphthol as reagent in Step E.

Elemental microanalysis:

|  | C% | H% | N% | S% |
| --- | --- | --- | --- | --- |
| calculated | 65.04 | 4.14 | 2.62 | 5.99 |
| found | 64.11 | 4.09 | 3.42 | 5.56 |

EXAMPLE 6

Sodium (E)-3-[5,6-dimethoxy-3-(4-methoxyphenoxy)-benzo[b]thiophen-2-yl]-2-phenyl-2-propenoate The procedure is as for Example 1 using phenylethanoic acid as reagent in Step F, and then as for Example 3.

Elemental microanalysis:

|  | C% | H% | S% |
|---|---|---|---|
| calculated | 64.46 | 4.37 | 6.62 |
| found | 63.81 | 4.25 | 5.98 |

EXAMPLE 7

(E)-3-{5,6-Dimethoxy-3-[(6-methoxy-2-naphthyl)-oxy]benzo[b]thiophen-2-yl]-2-phenyl-2-propenoic acid The procedure is as for Example 1 using the reagent of Example 5 in Step E, and the reagent of Example 6 in Step F.

Melting point: 274° C.

Elemental microanalysis:

|  | C% | H% | S% |
|---|---|---|---|
| calculated | 70.30 | 4.72 | 6.26 |
| found | 70.36 | 4.77 | 6.11 |

EXAMPLE 8

3-[5,6-Dimethoxy-3-(4-methoxyphenoxy)-benzo[b]thiophen-2-yl]-2-phenyl-propanoic acid The compound obtained in Example 6 after Step F is used as substrate, which is treated with a stream of hydrogen in the presence of 10% Pd/C in methanol for 24 hours. Filtration, at the end of the reaction, followed by chromatography over silica gel enables the expected product to be isolated.

Elemental microanalysis:

|  | C% | H% | S% |
|---|---|---|---|
| calculated | 67.23 | 5.21 | 6.90 |
| found | 67.02 | 5.22 | 6.75 |

EXAMPLE 9

Ethyl (E)-3-[5,6-dimethoxy-3-(4-methoxyphenoxy)-benzo[b]thiophen-2-yl]-propenoate 20 ml of a 1M solution of potassium tert-butylate in tetrahydrofuran are added dropwise at 0° C. under an inert atmosphere to a suspension of 0.02 mol of (ethoxycarbonylmethyl)triphenylphosphonium bromide in 90 ml of tetrahydrofuran. After the addition is complete and the mixture has returned to room temperature, 0.01 mol of the compound obtained in Step E of Example 1 diluted in 30 ml of tetrahydrofuran is added. After 12 hours, the reaction mixture is hydrolysed by the addition of 100 ml of a 1N HCl solution, and then extracted with ethyl acetate; the combined organic phases are washed with water and then with a saturated NaCl solution, dried over sodium sulphate, filtered and concentrated under reduced pressure. Chromatography over silica gel (pentane/ethyl acetate: 90/10) enables 2.78 g of the expected product to be isolated.

Melting point: 110° C.

Elemental microanalysis:

|  | C% | H% | S% |
|---|---|---|---|
| calculated | 63.75 | 5.35 | 7.74 |
| found | 63.76 | 5.42 | 7.33 |

EXAMPLE 10

(E)-3-[5,6-Dimethoxy-3-(4-methoxyphenoxy)-benzo[b]thiophen-2-yl]-2-propenoic acid The procedure is as for Example 2 using the product obtained in Example 9 as substrate.

Elemental microanalysis:

|  | C% | H% | S% |
|---|---|---|---|
| calculated | 62.17 | 4.69 | 8.30 |
| found | 62.15 | 4.69 | 8.46 |

EXAMPLE 11

Sodium (E)-3-[5,6-dimethoxy-3-(4-methoxyphenoxy)-benzo[b]thiophen-2-yl] propenoate The procedure is as for Example 3 using the product obtained in Example 10 as substrate.

Elemental microanalysis:

|  | C% | H% | S% |
|---|---|---|---|
| calculated | 58.82 | 4.20 | 7.85 |
| found | 58.86 | 4.25 | 7.38 |

EXAMPLE 12

Ethyl 3-[5,6-dimethoxy-3-(4-methoxyphenoxy)-benzo[b]thiophen-2-yl]-propanoate

A solution containing 0.8 mmol of the product obtained in Example 9 in 20 ml of methanol, and 0.2 g of 10% Pd/C is maintained at 40° C. for 24 hours under a stream of hydrogen. Filtration and concentration under reduced pressure and chromatography over silica gel (cyclohexane/ethyl acetate: 80/20) enable the expected product to be isolated.

EXAMPLE 13

Sodium 3-[5,6-dimethoxy-3-(4-methoxyphenoxy) benzo[b]thiophen-2-yl]-propanoate

The procedure is as for Example 2, and then as for Example 3 using the product obtained in Example 12 as substrate.

Elemental microanalysis:

|  | C% | H% | S% |
|---|---|---|---|
| calculated | 58.53 | 4.67 | 7.81 |
| found | 58.85 | 4.70 | 7.81 |

EXAMPLE 14

Ethyl 2-({[5,6-dimethoxy-3-(4-methoxyphenoxy)benzo[b]thiophen-2-yl]-methyl}anilino)acetate Step G: (5,6-Dimethoxy-3-(4-methyloxyphenoxy)-benzo[b]thiophen-2-yl)methanol 26 mmol of NaBH$_4$ are added at room temperature to a solution of 24 mmol of the compound obtained in Step E of Example 1 in 100 ml of methanol. After 2 hours' reaction, one equivalent of NaBH$_4$ is added to the reaction mixture. After 12 hours' reaction, the solution is concentrated and then diluted with ethyl acetate, washed with a 1N HCl solution, then with water and then with a saturated NaCl solution, subsequently dried over calcium sulphate, filtered and concentrated under reduced pressure. Chromatography over silica gel (dichloromethane/ethyl acetate: 95/5) enables 6.07 g of the expected product to be isolated.

Melting point: 132° C.

Step H: [2-Chloromethyl-5,6-dimethoxy-3-(4-methyloxyphenoxy)]-benzo[b]thiophene 0.63 ml of SOCl$_2$ is added dropwise at 0° C. to 4 mmol of the compound of Step G diluted in 10 ml of dichloromethane. After returning to room temperature, followed by heating to reflux of the dichloromethane for 6 hours, the reaction mixture is concentrated under reduced pressure, enabling 1.6 g of the expected product to be obtained in the form of an oil.

Elemental microanalysis:

|  | C% | H% | S% | Cl% |
|---|---|---|---|---|
| calculated | 59.26 | 4.70 | 8.79 | 9.72 |
| found | 58.90 | 4.75 | 8.85 | 11.52 |

Step I: Ethyl 2-({[5,6-dimethoxy-3-(4-methoxyphenoxy)benzo[b]thiophen-2-yl]-methyl}anilino)acetate A solution containing 6.5 mmol of the compound obtained in Step H, in 16 ml of dimethylformamide, 1.5 equivalents of N-phenylglycine ethyl ester and 1.5 equivalents of K$_2$CO$_3$ is heated at 80° C. for 18 hours. After the solvent has been removed by evaporation, the residue is diluted with ethyl acetate and the organic phase is washed with water and then with a saturated NaCl solution, dried over calcium sulphate, filtered and evaporated under reduced pressure. Chromatography over silica gel (toluene/ethyl acetate: 98/2) enables 2.56 g of the expected product to be isolated in the form of an oil.

EXAMPLE 15

2-({[5,6-Dimethoxy-3-(4-methyloxyphenoxy)benzo[b]thiophen-2-yl]methyl}anilino)ethanoic acid The procedure is as for Example 2 using the product obtained in Step I of Example 14 as substrate.

Elemental microanalysis:

|  | C% | H% | N% | S% |
|---|---|---|---|---|
| calculated | 65.12 | 5.25 | 2.92 | 6.69 |
| found | 65.53 | 5.47 | 3.02 | 6.33 |

EXAMPLE 16

Sodium 2-({[5,6-dimethoxy-3-(4-methyloxyphenoxy)benzo[b]thiophen-2-yl]methyl}anilino)acetate The procedure is as for Example 3 using the compound obtained in Example 15 as substrate.

Elemental microanalysis:

|  | C% | H% | N% | S% |
|---|---|---|---|---|
| calculated | 62.03 | 4.77 | 2.89 | 6.12 |
| found | 62.27 | 4.82 | 2.79 | 6.39 |

EXAMPLE 17

2-(Benzyl{[5,6dimethoxy-3-(4-methoxyphenoxy)benzo[b]thiophen-2-yl}amino)acetic acid The procedure is as for Example 14 using N-benzylglycine ethyl ester as reagent in Step I, and then as for Example 15.

EXAMPLE 18

Sodium 2-(benzyl{[5,6-dimethoxy-3-(4-methoxyphenoxy)benzo[b]-thiophen-2-yl]}amino)acetate The procedure is as for Example 16 using the product obtained in Example 17 as substrate.

Elemental microanalysis:

|  | C% | H% | N% | S% |
|---|---|---|---|---|
| calculated | 62.90 | 5.08 | 2.72 | 6.22 |
| found | 63.63 | 5.25 | 2.81 | 6.21 |

EXAMPLE 19

Sodium 2-({[5,6dimethoxy-3-(4-methoxyphenoxy)benzo[b]thiophen-2-yl]methyl}amino)acetate The procedure is as for Example 14 using glycine benzylate as reagent in Step I, and then as for the protocol of Example 15 and Example 16.

Elemental microanalysis:

|  | C% | H% | N% | S% |
|---|---|---|---|---|
| calculated | 56.46 | 4.74 | 3.29 | 7.54 |
| found | 56.88 | 4.70 | 3.24 | 6.95 |

EXAMPLE 20

Sodium 2-({[5,6-dimethoxy-3-(4-methoxyphenoxy)benzo[b]thiophen-2-yl]methyl}amino)benzoate The procedure is as for Example 19, using ethyl anthranilate as reagent in Step I.
Melting point: 250° C.
Mass spectrum: ESI$^{\pm}$: [M+H]$^{+}$=488; M+Na]$^{+}$=510.

EXAMPLE 21

Sodium 4-({[5,6-dimethoxy-3-(4-methoxyphenoxy)benzo[b]thiophen-2-yl]methyl}amino)benzoate The procedure is as for Example 19, using ethyl 4-aminobenzoate as reagent in Step I.
Elemental microanalysis:

|  | C% | H% | N% | S% |
|---|---|---|---|---|
| calculated | 61.59 | 4.55 | 2.87 | 6.58 |
| found | 60.95 | 4.31 | 2.99 | 6.54 |

EXAMPLE 22

Sodium 3-({[5,6-dimethoxy-3-(4-methoxyphenoxy)benzo[b]thiophen-2-yl]methyl}amino)benzoate The procedure is as for Example 9, using methyl 3-aminobenzoate as reagent in Step I.
Elemental microanalysis:

|  | C% | H% | N% | S% |
|---|---|---|---|---|
| calculated | 61.59 | 4.55 | 2.87 | 6.58 |
| found | 62.13 | 4.61 | 2.85 | 5.87 |

EXAMPLE 23

Sodium 2(S)-({[5,6-dimethoxy-3-(4-methoxyphenoxy)benzo[b]thiophen-2-yl]methyl}amino)-3-phenyl-propionate The procedure is as for Example 19, using benzyl (S)-phenylalanine as reagent in Step I.
Elemental microanalysis:

|  | C% | H% | N% | S% |
|---|---|---|---|---|
| calculated | 62.90 | 5.08 | 2.72 | 6.22 |
| found | 62.34 | 5.12 | 2.76 | 5.72 |

EXAMPLE 24

Methyl 2-[({[5,6-dimethoxy-3-(4-methoxyphenoxy)benzo[b]thiophen-2-yl]methyl}amino)sulphonyl]benzoate Step J: [2-Azidomethyl-5,6-dimethoxy-3-(4-methoxyphenoxy)]-benzo[b]thiophene A solution containing 41 mmol of the compound obtained in Step J of Example 14 and 78 mmol of sodium azide in 80 ml of dimethylformamide is stirred at room temperature for 48 hours. The reaction mixture is then concentrated under reduced pressure. The residue is diluted with ethyl acetate, and washed with water and then with a saturated NaCl solution. The organic phase is then dried over calcium sulphate, filtered and evaporated, enabling 15.4 g of the expected product to be obtained in the form of an oil.

Step K: [2-Aminomethyl-5,6-dimethoxy-3-(4-methoxyphenoxy)]-benzo[b]thiophene

A solution containing 41 mmol of the compound obtained in Step J and 1 g of Pd/C in 6.5 ml of chloroform and 300 ml of anhydrous methanol is placed under a hydrogen atmosphere at room temperature. After 12 hours, the reaction mixture is filtered and then concentrated under reduced pressure, enabling 14.5 g of the expected product to be obtained.
Melting point: 245° C.

Step L: Methyl 2-[({[5,6-dimethoxy-3-(4-methoxyphenoxy)benzo[b]thiophen-2-yl]-methyl}amino)sulphonyl]benzoate A solution containing 6.5 mmol of the compound obtained in Step K, 6.5 mmol of methyl 2-(chlorosulphonyl)benzoate, 15.7 mmol of N-methylmorpholine, in 50 ml of dichloromethane is stirred at room temperature. After 12 hours, the reaction mixture is washed with water and then with a saturated NaCl solution, dried over sodium sulphate and concentrated under reduced pressure. Chromatography over silica gel (dichloromethane/ethyl acetate: 98/2) enables 1.1 g of the expected product to be isolated.

EXAMPLE 25

2-[({[5,6-Dimethoxy-3-(4-methoxyphenoxy)benzo[b]thiophen-2-yl]methyl}amino)sulphonyl]benzoic acid The procedure is as for Example 2, using the compound obtained in Step L of Example 24 as substrate.
Elemental microanalysis:

|  | C% | H% | N% | S% |
|---|---|---|---|---|
| calculated | 56.70 | 4.38 | 2.64 | 12.11 |
| found | 56.79 | 4.77 | 2.66 | 11.86 |

EXAMPLE 26

Ammonium 2-[({[5,6-dimethoxy-3-(4-methoxyphenoxy)benzo-[b]thiophen-2-yl]methyl}amino)sulphonyl]benzoate Passage of the compound obtained in Example 25 over an HPLC column, followed by lyophilisation enables salt 26 to be obtained.
Elemental microanalysis:

|  | C% | H% | N% | S% |
|---|---|---|---|---|
| calculated | 54.93 | 4.79 | 5.12 | 11.73 |
| found | 54.97 | 4.82 | 5.00 | 12.23 |

EXAMPLE 27

Methyl 2-{[{[5,6-dimethoxy-3-(4-methoxyphenoxy)benzo[b]thiophen-2-yl]methyl}(methyl)amino]sulphonyl}benzoate 24 mg of sodium hydride are added at room temperature under an inert atmosphere to a solution of 0.38 g of the compound obtained in Step N of Example 24 in 5 ml of dimethylformamide. After 15 minutes' stirring, 0.15 g of methyl iodide diluted in 2 ml of dimethylformamide is added. After 18 hours' reaction at room temperature, the reaction mixture is concentrated. The residue is diluted in ethyl acetate, washed with a saturated NaHCO$_3$ solution, then with water and then with a saturated NaCl solution, dried over calcium sulphate, filtered and evaporated under reduced pressure. Chromatography over silica gel enables the expected product to be isolated.

EXAMPLE 28

Ethyl 2-[({[5,6-dimethoxy-3-(4-methoxyphenoxy) benzo[b]thiophen-2-yl]-methyl}amino)sulphonyl] acetate The procedure is as for Example 24, using ethyl 2-(chlorosulphonyl)ethanoate as reagent in Step L.

EXAMPLE 29

Sodium 2-[({[5,6-dimethoxy-3-(4-methoxyphenoxy) benzo[b]thiophen-2-yl]methyl}amino)sulphonyl] acetate The procedure is as for Example 3, replacing water with ethanol, and using the compound obtained in Example 28 as substrate.

Elemental microanalysis:

|  | C% | H% | N% | S% |
|---|---|---|---|---|
| calculated | 46.97 | 3.74 | 2.74 | 12.54 |
| found | 47.71 | 3.80 | 2.81 | 11.86 |

EXAMPLE 30

Ethyl 3-[5,6-dimethoxy-3-(4-methoxyphenoxy) benzo[b]thiophen-2-yl]-2-(4-pyridyl)-2-propanoate The compound obtained in Step F of Example 1 is subjected to the hydrogenation procedure described in Example 12.

EXAMPLE 31

Sodium 3-[5,6-dimethoxy-3-(4-methoxyphenoxy) benzo[b]thiophen-2-yl]-2-(4-pyridyl)-2-propanoate The procedure is as for Example 2 and then as for Example 3, using the product of Example 30 as substrate.

EXAMPLE 32

Sodium (E)-3-[5,6-dimethoxy-3-(3-pentylphenoxy) benzo[b]thiophen-2-yl]-2-(4-pyridinyl)-2-propenoate The procedure is as for Example 1 using 3-pentylphenol as reagent in Step E, followed by the procedure of Example 2 and Example 3.

Elemental microanalysis:

|  | C% | H% | N% | S% |
|---|---|---|---|---|
| calculated | 66.27 | 5.37 | 2.66 | 6.10 |
| found | 66.00 | 5.44 | 2.73 | 5.85 |

EXAMPLE 33

(E)-3-[5,6-Bis(benzyloxy)-3-(4-methoxyphenoxy) benzo[b]thiophen-2-yl]-2-(4-pyridinyl)-2-propenoic acid The procedure is as for Example 1 using 3,4-dibenzyloxycinnamic acid as starting material in Step A, and then as for Example 2.

EXAMPLE 34

(E)-3-[5,6-Dihydroxy-3-(4-methoxyphenoxy)benzo [b]thiophen-2-yl]-2-(4-pyridinyl)-2-propenoic acid The procedure is as for Example 33, but between Step E and Step F the following intermediate Step E' is carried out: 5,6-bis(benzyloxy)-3-(4-methoxyphenoxy)benzo[b] thiophene-2-carbaldehyde (obtained in Step E) is subjected to hydrogenolysis in the presence of 10% Pd/C in methanol. After 20 hours' reaction at room temperature, the reaction mixture is filtered and then concentrated under reduced pressure. Chromatography over silica gel permits isolation of the expected product, which is then subjected to the process described in Step F. The procedure is then in accordance with the protocol of Example 2.

EXAMPLE 35

(E)-3-[5,6-Bis(benzyloxy)-3-(4-benzyloxyphenoxy) benzo[b]thiophen-2-yl]-2-(4-pyridinyl)-2-propenoic acid The procedure is as for Example 33 using 4-benzyloxyphenol as reagent in Step E, and then as for Example 2.

EXAMPLE 36

(E)-3-[5-Chloro-4,7-dimethoxy-3-(4-methoxyphenoxy)benzo[b]thiophen-2-yl]-2-(4-pyridinyl)-2-propenoic acid The procedure is as for Example 1, using 3-chloro-2,5-dimethoxycinnamic acid as starting material in Step A, followed by the protocol described in Example 2.

EXAMPLE 37

(E)-3-[6,7-Dichloro-3-(4-methoxyphenoxy)benzo[b] thiophen-2-yl]-2-(4-pyridinyl)-2-propenoic acid The procedure is as for Example 1, using 4,5-dichlorocinnamic acid as starting material in Step A, followed by the protocol described in Example 2.

EXAMPLE 38

(E)-3-[5,6-Dimethoxy-3-(2,4-difluorophenoxy)benzo [b]thiophen-2-yl]-2-(4-pyridinyl)-2-propenoic acid The procedure is as for Example 1, using 2,4-difluorophenol as reagent in Step E, followed by the protocol described in Example 2.

EXAMPLE 39

(E)-3-[5,6Dimethoxy-3-(3-pyridinyloxy)benzo[b]thiophen-2-yl]-2-(4-pyridinyl)-2-propenoic acid The procedure is as for Example 1, using 3-hydroxypyridine as reagent in Step E, followed by the protocol described in Example 2.

EXAMPLE 40

(E)-3-{3-[(4,6-Dimethyl-2-pyrimidinyl)oxy]-6methoxy-1-benzofuran-2-yl}-2-(4-pyridinyl)-2-propenoic acid Step 1: 3-[4,6-Dimethyl-2-pyrimidinyl)oxy]-6-methoxy-2-benzofuran-2-carbaldehyde The procedure is as Step E for Example 1 using 3-hydroxy-6-methoxy-1-benzofuran-2-carbaldehyde as substrate and 2-chloro-4,6-dimethyl-pyrimidine as reagent.

Step 2: (E)-3-{3-[4,6-Dimethyl-2-pyrimidinyl)oxy]-6-methoxy-1-benzofuran-2-yl}-2-(4-pyridinyl)-2-propenoic acid The procedure is as Step F for Example 1 using the product obtained in Step I as substrate, followed by the protocol described in Step G of Example 2.

EXAMPLE 41

(E)-3-[5,6-Dimethoxy-3-(4-methoxyphenoxy)-1H-2-indolyl]-2-(4-pyridinyl)-2-propenoic acid The procedure is as for Example 1, from Step E to Step F, using 3-bromo-5,6-dimethoxy-1H-2-indolecarbaldehyde as substrate in Step E, followed by the protocol described in Example 2.

EXAMPLE 42

(E)-3-[5,6-Dimethoxy-3-[(4-methoxyphenyl)sulphanyl]benzo[b]thiophen-2-yl]-2-(4-pyridinyl)-2-propenoic acid The procedure is as for Example 1, using 4-methoxybenzenethiol as reagent in Step E, followed by the protocol described in Example 2.

EXAMPLE 43

Sodium (E)-3-[5,6-bis(benzyloxy)-3-(4-methoxyphenoxy)benzo[b]thiophen-2-yl]-2-(4-pyridinyl)-2-propenoate The procedure is as for Example 3 using the product of Example 33 as substrate.

Melting point: >260° C.
Elemental microanalysis:

|  | C% | H% | N% | S% |
|---|---|---|---|---|
| calculated | 69.69 | 4.43 | 2.20 | 5.03 |
| found | 70.10 | 4.40 | 2.25 | 4.66 |

EXAMPLE 44

Sodium (E)-3-[5,6-bis(benzyloxy)-3-(4-benzyloxyphenoxy)benzo-[b]thiophen-2-yl]-2-(4-pyridinyl)-2-propenoate The procedure is as for Example 3 using the product of Example 35 as substrate.

Melting point: >260° C.
Elemental microanalysis:

|  | C% | H% | N% | S% |
|---|---|---|---|---|
| calculated | 72.36 | 4.52 | 1.96 | 4.49 |
| found | 72.51 | 4.54 | 2.04 | 4.25 |

EXAMPLE 45

Sodium (E)-3-[6,7-dichloro-3-(4-methoxyphenoxy)benzo[b]thiophen-2-yl]-2-(4-pyridinyl)-2-propenoate The procedure is as for Example 3 using the product of Example 37 as substrate.

Elemental microanalysis:

|  | C% | H% | N% | S% | Cl% |
|---|---|---|---|---|---|
| calculated | 55.88 | 2.85 | 2.83 | 6.49 | 14.34 |
| found | 56.27 | 2.95 | 2.91 | 6.80 | 14.45 |

EXAMPLE 46

Sodium (E)-3-[3-(4-chlorophenoxy)-5,6-dimethoxybenzo[b]thiophen-2-yl]-2-(4-pyridinyl)-2-propenoate The procedure is as for Example 1 using 4-chlorophenol as reagent in Step E, followed by the protocol described in Example 2 and then Example 3.

Elemental microanalysis:

|  | C% | H% | N% | S% | Cl% |
|---|---|---|---|---|---|
| calculated | 58.84 | 3.50 | 2.86 | 6.54 | 7.24 |
| found | 59.33 | 3.53 | 2.93 | 6.28 | 7.60 |

EXAMPLE 47

Sodium 4-({2-[(E)-2-sodiumcarboxy-2-(4-pyridinyl)ethenyl]-5,6-dimethoxy-1-benzo[b]thiophen-3-yl}oxy)benzoate The procedure is as for Example 1 using methyl 4-hydroxybenzoate as reagent in Step E, followed by the protocol described in Example 2 and then Example 3.

Elemental microanalysis:

|  | C% | H% | N% | S% |
|---|---|---|---|---|
| calculated | 57.58 | 3.29 | 2.69 | 6.15 |
| found | 57.20 | 3.07 | 2.65 | 5.63 |

EXAMPLE 48

Sodium (E)-3-[5chloro-4,7-dimethoxy-3-(4-methoxyphenoxy)-benzo[b]thiophen-2-yl]-2-(4-pyridinyl)-2-propenoate The procedure is as for Example 3 using the product of Example 36 as substrate.

Elemental microanalysis:

|  | C% | H% | N% | S% | Cl% |
|---|---|---|---|---|---|
| calculated | 57.75 | 3.68 | 2.69 | 6.82 | 6.17 |
| found | 57.93 | 3.61 | 2.67 | 6.84 | 6.10 |

EXAMPLE 49

Sodium (E)-3-[5,6-dimethoxy-3-(2,4-difluorophenoxy)benzo[b]thiophen-2-yl]-2-(4-pyridinyl)-2-propenoate The procedure is as for Example 3 using the product of Example 38 as substrate.
Elemental microanalysis:

|  | C% | H% | N% | S% |
|---|---|---|---|---|
| calculated | 58.66 | 3.28 | 2.85 | 6.52 |
| found | 58.90 | 3.16 | 2.95 | 6.49 |

EXAMPLE 50

3-(E)-{3-[4-(2-(Dimethylamino)ethoxy)-phenoxy]-5,6-dimethoxybenzo[b]thiophen-2-yl}-2-phenyl-2-propenoic acid The procedure is as for Example 1 using 2-(dimethylamino)ethoxyphenol as reagent in Step E, and using phenylethanoic acid as reagent in Step F, followed by the protocol described in Example 2.
Elemental microanalysis:

|  | C% | H% | N% | S% |
|---|---|---|---|---|
| calculated | 58.10 | 4.70 | 2.17 | 4.97 |
| found | 57.63 | 4.60 | 2.23 | 4.84 |

EXAMPLE 51

Sodium (E)-3-[5,6-dimethoxy-3-(3-methoxyphenoxy)benzo[b]thiophen-2-yl]-2-(4-pyridinyl)-2-propenoate The procedure is as for Example 1, using 3-methoxyphenol as reagent in Step E, followed by the protocol described in Example 2, and then Example 3.
Elemental microanalysis:

|  | C% | H% | N% | S% |
|---|---|---|---|---|
| calculated | 61.85 | 4.15 | 2.89 | 6.60 |
| found | 61.66 | 4.21 | 2.89 | 6.36 |

EXAMPLE 52

Sodium (E)-3-[3-(4-trifluoromethylphenoxy)-5,6-dimethoxybenzo[b]thiophen-2-yl]-2-(4-pyridinyl)-2-propenoate The procedure is as for Example 1, using 4-trifluoromethylphenol as reagent in Step E, followed by the protocol described in Example 2, and then Example 3.

Elemental microanalysis:

|  | C% | H% | N% | S% |
|---|---|---|---|---|
| calculated | 57.36 | 3.27 | 2.68 | 6.13 |
| found | 57.43 | 2.78 | 2.72 | 6.33 |

EXAMPLE 53

Sodium (E)-3-[5,6-dimethoxy-3-(2-methoxyphenoxy)benzo[b]thiophen-2-yl]-2-(4-pyridinyl)-2-propenoate The procedure is as for Example 1, using 2-methoxyphenol as reagent in Step E, followed by the protocol described in Example 2, and then Example 3.

Mass spectrum: FAB: [M+H]$^+$: m/z=486; [M−Na+2H]$^+$: m/z=464, [M−H+2Na]$^+$: m/z=508.

EXAMPLE 54

Sodium (E)-3-{3-[4-sodiumcarboxymethyl)phenoxy]-5,6-dimethoxy-1-benzo[b]thiophen-2-yl}-2-(4-pyridinyl)-2-propenoate The procedure is as for Example 1 using ethyl 4-hydroxyphenylethanoate as reagent in Step E, followed by the protocol described in Example 2, and then Example 3.
Elemental microanalysis:

|  | C% | H% | N% | S% |
|---|---|---|---|---|
| calculated | 58.32 | 3.58 | 2.62 | 5.99 |
| found | 58.38 | 3.65 | 2.65 | 5.80 |

EXAMPLE 55

Sodium (E)-3-[5,6-dimethoxy-3-(4-(trifluoromethoxy)phenoxybenzo[b]thiophen-2-yl]-2-(4-pyridinyl)-2-propenoate The procedure is as for Example 1, using 4-(trifluoromethoxy)phenol as reagent in Step E, followed by the protocol described in Example 2, and then Example 3.
Elemental microanalysis:

|  | C% | H% | N% | S% |
|---|---|---|---|---|
| calculated | 55.66 | 3.18 | 2.60 | 5.94 |
| found | 56.07 | 3.00 | 2.64 | 6.04 |

EXAMPLE 56

Sodium (E)-3-{3-[4-(acetylamino)phenoxy]-5,6-dimethoxybenzo[b]thiophen-2-yl}-2-(4-pyridinyl)-2-propenoate The procedure is as for Example 1, using 4-(acetylamino)phenyl as reagent in Step E, followed by the protocol described in Example 2, and then Example 3.

Mass spectrum: FAB: [M+H]$^+$: m/z=513; [M+Na]$^+$; m/z=535.

EXAMPLE 57

Sodium (E)-3-[5,6-dimethoxy-3-(4-methoxyphenyl)-1-(4-pyridinylmethyl-1H-indol-2-yl]-2-propenoate The procedure is as for Example 1, from Steps B to D and then Step F, using ethyl 5,6-dimethoxy-3-(4-methoxyphenyl)-1-(4-pyridinylmethyl)-2-indolinecarboxylate as substrate in Step B, and using ethyl 2-(triphenylphosphoranylidene)acetate as reagent in Step F. The protocol described in Example 2 and Example 3 is then followed.

Elemental microanalysis:

|  | C% | H% | N% |
|---|---|---|---|
| calculated | 66.95 | 4.97 | 6.01 |
| found | 66.18 | 4.76 | 6.01 |

EXAMPLE 58

3-(E)-[5,6-Bis(benzyloxy)-3-(3-pyridinyloxy)-benzo[b]thiophen-2-yl]-2-(4-pyridinyl)-2-propenoic acid The procedure is as for Example 1, using 3,4-bis(benzyloxy)cinnamic acid as substrate in Step A and using 3-hydroxypyridine as reagent in Step E, followed by the protocol described in Example 2.

Melting point: 256° C.

Elemental microanalysis:

|  | C% | H% | N% | S% |
|---|---|---|---|---|
| calculated | 71.66 | 4.47 | 4.77 | 5.47 |
| found | 71.59 | 4.58 | 4.78 | 5.10 |

EXAMPLE 59

3-(E)-{5,6-Bis(benzyloxy)-3-[4-(hydroxy)phenoxy]-benzo[b]-thiophen-2-yl}-2-(4-pyridinyl)-2-propenoic acid Step 1: 5,6-Bis(benzyloxy)-3-[4-(4-pyridinyloxy)phenoxy]-benzo[b]thiophene-2-carbaldehyde The procedure is as for Example 1, Steps A to E, using 3,4-bis(benzyloxy)cinnamic acid as substrate in Step A and using 4-(4-pyridinyloxy)phenol as reagent in Step E.

Step 2: Ethyl (E)-3-{3-[4-(acetyloxy)phenoxy]-5,6-bis(benzyloxy)-benzo[b]thiophen-2-yl}-2-(4-pyridinyl)-2-propenoate The procedure is as for Step F of Example 1 using the product obtained in the preceding Step 1 as starting material.

Step 3: 3-(E)-{5,6-Bis(benzyloxy)-3-[4-(hydroxy)phenoxy]-benzo[b]thiophen-2-yl}-2-(4-pyridinyl)-2-propenoic acid The procedure is as for Example 2 using the product obtained in the preceding Step 2.

Melting point: 256° C.

Elemental microanalysis:

|  | C% | H% | N% | S% |
|---|---|---|---|---|
| calculated | 71.87 | 4.52 | 2.33 | 5.33 |
| found | 71.40 | 4.58 | 2.35 | 4.93 |

EXAMPLE 60

3-(E)-{5,6-Bis(benzyloxy)-3-[6-(methyl)pyridinyl-3-oxy]-benzo[b]thiophen-2-yl}-2-(4-pyridinyl)-2-propenoic acid The procedure is as for Example 1, using 3,4-bis(benzyloxy)cinnamic acid as substrate in Step A and using 2-methyl-5-hydroxypyridine as reagent in Step E, followed by the protocol described in Example 2.

Melting point: 228° C.

Elemental microanalysis:

|  | C% | H% | N% | S% |
|---|---|---|---|---|
| calculated | 71.98 | 4.70 | 4.66 | 5.34 |
| found | 72.19 | 4.81 | 4.70 | 4.94 |

EXAMPLE 61

3-(E)-{6-Benzyloxy-3-[4-(benzyloxy)phenoxy]-5-methoxybenzo[b]thiophen-2-yl}-2-(4-pyridinyl)-2-propenoic acid The procedure is as for Example 1, using 4-benzyloxy-3-methoxycinnamic acid as substrate in Step A and using 4-(benzyloxy)phenol as reagent in Step E, followed by the protocol described in Example 2.

Melting point: 216° C.

Elemental microanalysis:

|  | C% | H% | N% | S% |
|---|---|---|---|---|
| calculated | 72.18 | 4.75 | 2.27 | 5.21 |
| found | 71.92 | 4.56 | 2.32 | 5.10 |

EXAMPLE 62

3-(E)-{5-Benzyloxy-3-[4-(benzyloxy)phenoxy]-6-methoxybenzo[b]thiophen-2-yl}-2-(4-pyridinyl)-2-propenoic acid The procedure is as for Example 61 using 3-benzyloxy-4-methoxycinnamic acid as starting material.

Melting point: 210° C.

EXAMPLE 63

Sodium (E)-3-[5,6-bis(benzyloxy)-3-(6-quinolinyloxy)benzo[b]thiophen-2-yl]-2-(4-pyridinyl)-2-propenoate Step 1: 3-(E)-[5,6-Bis(benzyloxy)-3-(6-quinolinyloxy)benzo[b]thiophen-2-yl]-2-(4-pyridinyl)-2-propenoic acid The procedure is as for Example 1 using 3,4-bis(benzyloxy)cinnamic acid as substrate in Step A and using 6-hydroxyquinoline as reagent in Step E, followed by the protocol described in Example 2.

Step 2: Sodium (E)-3-[5,6-bis(benzyloxy)-3-(6-quinolinyloxy)benzo[b]thiophen-2-yl]-2-(4-pyridinyl)-2-propenoate The procedure is as for Example 3 using the product obtained in Step I as substrate.

Elemental microanalysis:

|  | C% | H% | N% | S% |
|---|---|---|---|---|
| calculated | 71.11 | 4.13 | 4.25 | 4.87 |
| found | 71.36 | 4.22 | 4.31 | 4.46 |

EXAMPLE 64

Sodium (E)-3-{5,6-bis(benzyloxy)-3-[4-(1H-imidazol-1-yl)phenoxy]-benzo[b]thiophen-2-yl}-2-(4-pyridinyl)-2-propenoate The procedure is as for Example 1 using 3,4-bis(benzyloxy)cinnamic acid as substrate in Step A and using 4-(1H-imidazol-1-yl)phenol as reagent in Step E, followed by the protocol described in Example 2 and then Example 3.

Elemental microanalysis:

|  | C% | H% | N% | S% |
|---|---|---|---|---|
| calculated | 69.53 | 4.19 | 6.24 | 4.76 |
| found | 69.27 | 4.25 | 6.29 | 4.62 |

EXAMPLE 65

(E)-3-{5,6-Bis(benzyloxy)-3-[(6-methoxy-3pyridinyloxy]-benzo[b]thiophen-2-yl}-2-(4-pyridinyl)-2-propenoic acid The procedure is as for Example 1, using 3,4-bis(benzyloxy)cinnamic acid as substrate in Step A and using 6-methoxy-3-pyridinol as reagent in Step E, followed by the protocol described in Example 2.

Melting point: 188° C.

Elemental microanalysis:

|  | C% | H% | N% | S% |
|---|---|---|---|---|
| calculated | 70.12 | 4.58 | 4.54 | 5.20 |
| found | 69.77 | 4.67 | 4.58 | 4.82 |

EXAMPLE 66

(E)-3-{5,6-Bis(benzyloxy)-3-[4-(4-pyridinyl)phenoxy-benzo[b]thiophen-2-yl}-2-(4-pyridinyl)-2-propenoic acid The procedure is as for Example 65 using 4-(4-pyridinyl)phenol as reagent in Step E.

Mass spectrum: FAB: [M+H]$^+$: m/z=663.

EXAMPLE 67

Sodium (E)-3-[5-benzyloxy-6-methoxy-3-(3pyridinyloxy-benzo[b]thiophen-2-yl]-2-(4-pyridinyl)-2-propenoate Step 1: (E)-3-[5-Benzyloxy-6-methoxy-3-(3-pyridinyloxy) benzo [b]thiophen-2-yl]-2-(4-pyridinyl)-2-propenoic acid The procedure is as for Example 1 using 3-benzyloxy-4-methoxycinnamic acid as substrate in Step A and using 3-pyridinol as reagent in Step E, followed by the protocol described in Example 2.

Step 2: (E)-3-[5-Benzyloxy-6-methoxy-3-(3-pyridinyloxy) benzo[b]thiophen-2-yl]-2-(4-pyridinyl)-2-propenoic acid The procedure is as for Example 3 using the product obtained in Step I as substrate.

Elemental microanalysis:

|  | C% | H% | N% | S% |
|---|---|---|---|---|
| calculated | 65.41 | 3.97 | 5.26 | 6.02 |
| found | 65.25 | 3.99 | 5.24 | 5.84 |

EXAMPLE 68

(E)-3-{3-[(1-Hydroxy-2-oxo-1,2-dihydro-4-pyridinyloxy]-5,6-dimethoxy-benzo[b]thiophen-2-yl}-2-(4-pyridinyl)-2-propenoic acid The procedure is as for Example 1 using 1,4-dihydroxy-2-oxo-1,2-dihydropyridine as reagent in Step E, followed by the protocol described in Example 2.

EXAMPLE 69

3-(E)-{5,6-Dimethoxy-3-[(2-oxo-2,3-dihydro-1H-indol-5-yl)oxy]-benzo[b]thiophen-2-yl}-2-(4-pyridinyl)-2-propenoic acid The procedure is as for Example 1 using 5-hydroxy-1,3-dihydro-2H-indol-2-one as reagent in Step E.

EXAMPLE 70

3-(E)-[3-(1H-Benzimidazol-5-yloxy)-5,6-dimethoxy-benzo[b]thiophen-2-yl]-2-(4-pyridinyl)-2-propenoic acid The procedure is as for Example 1 using 5-hydroxy-1H-benzimidazole as reagent in Step E, followed by the protocol of Example 2.

EXAMPLE 71

3-(E)-[3-(1H-Indol-5-yloxy)-5,6-dimethoxy-benzo[b]thiophen-2-yl]-2-(4-pyridinyl)-2-propenoic acid The procedure is as for Example 1 using 5-hydroxy-1H-indole as reagent in Step E, followed by the protocol of Example 2.

EXAMPLE 72

3-(E)-[5,6-Dimethoxy-3-(1,2,3,4-tetrahydro-6-quinolinyloxy)-benzo[b]thiophen-2-yl]-2-(4-pyridinyl)-2-propenoic acid The procedure is as for Example 1 using 1,2,3,4-tetrahydro-6-quinolinol as reagent in Step E, followed by the protocol of Example 2.

EXAMPLE 73

Ethyl (E)-3-[5,6-dimethoxy-3-(4-methoxyanilino) benzo[b]thiophen-2-yl]-2-(4-pyridinyl)-2-propenoate The procedure is as for Example 1 using p-anisidine as reagent in Step E.

EXAMPLE 74

Ethyl (E)-3-[5,6-bis(benzyloxy)-3-(4-methoxyanilino)benzo[b]thiophen-2-yl]-2-(4-pyridinyl)-2-propenoate The procedure is as for Example 1 using 3,4-bis(benzyloxy)-cinnamic acid as substrate in Step A and using p-anisidine as reagent in Step E.

EXAMPLE 75

Ethyl (E)-3-[5,6 dimethoxy-3-(4-methoxyphenoxy)-benzo[b]thiophen-2-yl]-2-(4-methylphenyl)-2-propenoate The procedure is as for Example 1, using ethyl 4-methylphenylacetate as reagent in Step F.

EXAMPLE 76

Ethyl (E)-3-[5,6-dimethoxy-3-[4-methoxyphenoxy)-benzo[b]thiophen-2-yl]-2-(3-thienyl)-2-propenoate The procedure is as for Example 1, using ethyl 3-thiopheneacetate as reagent in Step F.

EXAMPLE 77

Ethyl (E)-3-[5,6-(1,3,4,6-tetrahydro-2,5-benzodioxin-3,4-diyl)-3-(4-methoxyphenoxy)-benzo[b]thiophen-2-yl]-2-(4-pyridinyl)-2-propenoate The procedure is as for Example 1, using 3,4-(1,3,4,6-tetrahydro-2,5-benzodioxin-3,4-diyl)cinnamic acid as substrate in Step A, which is obtained by the addition of dibromo-o-xylene to 3,4-dihydroxycinnamic acid.

EXAMPLE 78

Ethyl (E)-3-[3phenyl-9-(4methoxyphenoxy)-3,4-dihydro-2H-thieno[2,3-h][1,5]benzodioxepin-8-yl]-2-(4-pyridinyl)-2-propenoate The procedure is as for Example 1 using (E)-3-(3-phenyl-3,4-dihydro-2H-15-benzodioxepin-7-yl)-2-propenoic acid as substrate in Step A.

EXAMPLE 79

Ethyl (E)-3-[8-(4-methoxyphenoxy)-2,3diphenyl-2,3-dihydrothieno[2,3-g][1,4]benzodioxin-7-yl]-2-(4-pyridinyl)-2-propenoate The procedure is as for Example 1 using (E)-3-(2.3-diphenyl-2,3-dihydro-1,4-benzodioxin-6-yl)-2-propenoic acid as substrate in Step A.

Pharmacological Study of the Compounds of the Invention

EXAMPLE 80

Inhibition of the Activity of PAI-1

Inhibition of the activity of PAI-1 was effected in vitro in microplate wells in which the formation and then breakdown of a fibrin clot is monitored continuously by measurement of its turbidity using a spectrophotometer. To do so, using a 50 mM phosphate buffer, pH 7.4 containing 0.05% of bovine serum albumin as diluent, 50 μl of the inhibitor is placed in the presence of 50 μl of a 2 nM solution of recombinant active human PAI-1 for 5 minutes at room temperature. 50 μl of a 0.42 nM solution of tissue plasminogen activator, 50 μl of an 800 nM solution of human plasminogen and 50 μl of a 2 g/liter solution of fibrinogen are then added and the fibrin formation is triggered by the addition of 50 μl of 14 nM purified human thrombin. In the absence of the product, inhibition of breakdown two hours after the start of fibrin formation is measured by the absorbance of the clot and represents 100% of the PAI-1 activity. In the absence of the product and of PAI-1, breakdown is measured by the absorbance of the broken-down clot and represents 0% of the PAI-1 activity. The concentration of product that inhibits PAI-1 activity by 50% is determined by measuring the absorbance of the clot two hours after fibrin formation in the presence of PAI-1 and of an increasing concentration of the product. The $IC_{50}$ of the compounds of this invention and of the reference product, XR 5082, are described in Table 1. The results demonstrate that the compounds of the present invention exhibits a better fibrinolytic activity.

TABLE 1

| | fibrinolytic activity |
|---|---|
| Example | $IC_{50}$ (μM) |
| 43 | 13 |
| 44 | 7 |
| 66 | 2,2 |
| 67 | 5 |
| XR 5082 | 190 |

EXAMPLE 81

Pharmaceutical Composition

Formulation for the preparation of 1000 tablets containing a dose of 10 mg:

| Compound of Example | 10 g |
|---|---|
| Hydroxypropyl cellulose | 2 g |
| Polyvinylpyrrolidone | 2 g |
| Wheat starch | 10 g |
| Lactose | 100 g |
| Magnesium stearate | 3 g |

We claim:
1. A compound selected from the group consisting of those of the formula (I):

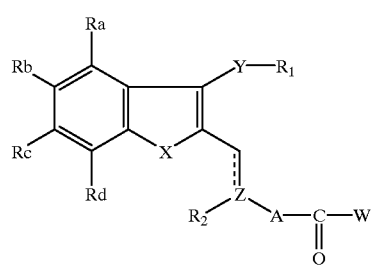

in which:
X represents sulphur,
Y represents oxygen, sulphur, $NR_3$, $R_3$ being hydrogen, linear or branched ($C_1$–$C_6$)alkyl, linear or branched ($C_1$–$C_6$)acyl, aryl, aryl-($C_1$–$C_6$)alkyl in which the alkyl moiety is linear or branched, or heteroaryl-($C_1$–$C_6$) alkyl in which the alkyl moiety is linear or branched, Z represents nitrogen when the bond that links it to the adjacent carbon is single (—), or Z may be carbon or CH depending on whether the bond that links it to the adjacent carbon is single (—) or double (═), A represents a single bond, ($C_1$–$C_6$)alkylene (optionally substituted by one or more linear or branched ($C_1$–$C_6$) alkyl, aryl, aryl-($C_1$–$C_6$)alkyl in which the alkyl moiety is linear or branched, cycloalkyl, or by a heterocycle), arylene, cycloalkylene, a heterocycle, or the —$SO_2$—$R_4$— ($SO_2$ moiety being linked to Z) in which $R_4$ is selected from linear or branched ($C_1$–$C_6$)alkylene, arylene, aryl-($C_1$–$C_6$)alkylene in which the alkylene moiety is linear or branched, cycloalkylene, and a heterocycle, W represents hydroxy, linear or branched ($C_1$–$C_6$) the alkoxy, aryloxy, aryl-($C_1$–$C_6$)alkoxy in which alkoxy moiety is linear or branched, cycloalkyloxy, a heterocycle bonded to an oxygen, amino (which may itself be substituted by one or two identical or different groups, each independently of the other selected from linear or branched ($C_1$–$C_6$)alkyl, aryl, aryl-($C_1$–$C_6$)alkyl in which alkyl moiety is linear or branched, and cycloalkyl), or hydroxyamino, Ra, Rb, Rc, Rd, which may be the same or different, each independently of the others represents hydrogen, halogen, hydroxy, cyano, nitro, linear or branched ($C_1$–$C_6$)alkyl, linear or branched ($C_1$–$C_6$)alkoxy, linear or branched ($C_1$–$C_6$)acyl, carboxy, linear or branched ($C_1$–$C_6$)alkoxy-carbonyl, linear or branched ($C_1$–$C_6$) trihaloalkyl, amino (which may be optionally substituted by one or two identical or different groups, each independently of the other selected from linear or branched ($C_1$–$C_6$)alkyl, aryl, and aryl-($C_1$–$C_6$)alkyl in which the alkyl moiety is linear or branched), aryloxy, aryl-($C_1$–$C_6$)alkoxy in which the alkoxy moiety is linear or branched, heteroaryloxy, or heteroaryl-($C_1$–$C_6$)alkoxy in which the alkoxy moiety is linear or branched, or Ra+Rb, Rb+Rc or Rc+Rd represents a formula -$U_1$-V-$U_2$ (in which case each of the remaining groups Ra, Rb, Rc, Rd takes one of the other meanings given above), wherein $U_1$ and $U_2$, represent oxygen, V represents linear ($C_1$–$C_4$)alkylene, which may be optionally substituted by one or more linear or branched ($C_1$–$C_6$)alkyl, aryl, aryl-($C_1$–$C_6$)alkyl in which the alkyl moiety is linear or branched, or V represents a group of formula

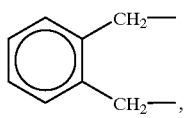

with the proviso that Ra, Rb, Rc and Rd cannot simultaneously represent hydrogen, $R_1$ represents:
aryl substituted by one to five identical or different substituents, each independently of the others selected from halogen, hydroxy, cyano, nitro, carboxy, linear or branched ($C_1$–$C_6$)alkyl, linear or branched ($C_1$–$C_6$)alkoxy, linear or branched ($C_1$–$C_6$) acyl, linear or branched ($C_1$–$C_6$)alkoxycarbonyl, trihalo-($C_1$–$C_6$)alkyl (in which the alkyl moiety is linear or branched and may be optionally substituted by hydroxy), trihalo-($C_1$–$C_6$)-alkoxy in which the alkoxy moiety is linear or branched, amino (which may be optionally substituted by one or two linear or branched ($C_1$–$C_6$)alkyl, one of which alkyl may be itself optionally substituted by a group selected from amino, linear or branched ($C_1$–$C_6$)alkylamino, and di-($C_1$–$C_6$)alkylamino in which the alkyl moieties are each linear or branched), amino-($C_1$–$C_6$)alkoxy in which the alkoxy moiety is linear or branched (and the amino moiety of which may be itself substituted by one or two, identical or different, linear or branched ($C_1$–$C_6$)alkyl), ($C_1$–$C_6$)alkoxycarbonyl-($C_1$–$C_6$)alkyl in which alkoxy and the alkyl moieties are each linear or branched, linear or branched ($C_1$–$C_6$)-alkylcarbonylamino, aryl-($C_1$–$C_6$)alkyl in which the alkyl moiety is linear or branched, aryloxy, aryl-($C_1$–$C_6$)alkoxy in which the alkoxy moiety is linear or branched, arylamino, aryl-($C_1$–$C_6$) alkylamino in which the alkyl moiety is linear or branched, arylsulphanyl, aryl-($C_1$–$C_6$) alkylsulphanyl in which the alkyl moiety is linear or branched, heteroaryl, heteroaryl-($C_1$–$C_6$)alkyl in which the alkyl moiety is linear or branched, heteroaryloxy, heteroaryl-($C_1$–$C_6$)alkoxy in which the alkoxy moiety is linear or branched, heteroarylamino, heteroaryl-($C_1$–$C_6$)alkylamino in which the alkyl moiety is linear or branched, heteroarylsulphanyl, and heteroaryl-($C_1$–$C_6$) alkylsulphanyl in which the alkyl moiety is linear or branched, or a group of formula

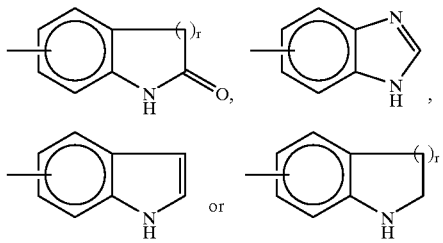

wherein r is 1 or 2, or
1-hydroxy-2(1H)-pyridinone, or
optionally substituted heteroaryl, it being understood that heteroaryl is selected from the group consisting of pyridine, pyrimidine, quinoline, isoquinoline, 1,3-dihydro2H-pyrrolopyridin-2-one, 3H-imidazopyridine, 1H-pyrrolopyridine, 1,2,3,4-tetrahydronaphthpyridine, and 2,3-dihydro-1H-pyrrolopyridine, $R_2$ represents hydrogen, linear or branched ($C_1$–$C_6$)alkyl, aryl, aryl-($C_1$–$C_6$)alkyl in which the alkyl moiety is linear or branched, cycloalkyl, an optionally substituted heterocycle, or heterocycle bonded to a linear or branched ($C_1$–$C_6$)-alkyl, an isomer or a pharmaceutically-acceptable acid or base addition salt thereof.

2. A compound of claim 1, wherein Y represents oxygen, or its isomer or an addition salt thereof with a pharmaceutically-acceptable acid or base.

3. A compound of claim 1, wherein $R_1$ represents optionally substituted phenyl, optionally substituted pyridinyl, or optionally substituted quinolyl, an isomer or a addition salt thereof with a pharmaceutically-acceptable acid or base.

4. A compound of claim 1, wherein $R_2$ represents optionally substituted aryl, or optionally substituted heterocycle, an isomer or an addition salt thereof with a pharmaceutically-acceptable acid or base.

5. A compound of claim 1, wherein $R_2$ represents pyridinyl, an isomer or a also addition salt thereof with a pharmaceutically-acceptable acid or base.

6. A compound of claim 1, wherein

X represents sulphur,

Y represents oxygen, $R_1$ represents optionally substituted phenyl, or optionally substituted pyridinyl, A represents a single bond when Z represents carbon, or CH, or its isomer or an addition salt thereof with a pharmaceutically-acceptable acid or base.

7. A compound of claim 1,

X represents sulphur,

Y represents oxygen, $R_1$ represents phenyl, optionally substituted by one group as defined for formula (I), A represents $(C_1-C_6)$alkylene (optionally substituted by linear or branched $(C_1-C_6)$-alkyl, aryl, aryl-$(C_1-C_6)$ alkyl in which alkyl moiety is linear or branched), or arylene when Z represents nitrogen, or its isomer or an addition salt thereof with a pharmaceutically-acceptable acid or base.

8. A compound of claim 1, which is selected from (E)-3-[5,6-dimethoxy-3-(4-methoxyphenoxy)benzo[b]thiophen-2-yl]-2-(4-pyridinyl)-2-propenoic acid or an addition salt with a pharmaceutically-acceptable acid or base.

9. A compound of claim 1, which is selected from (E)-3-[5,6-bis(benzyloxy)-3-(4-methoxyphenoxy)benzo[b]thiophen-2-yl]-2-(4-pyridinyl)-2-propenoic acid or an addition salt with a pharmaceutically-acceptable acid or base.

10. A compound of claim 1, which is selected from (E)-3-[5,6-bis(benzyloxy)-3-(4-benzyloxyphenoxy)benzo[b]thiophen-2-yl]-2-(4-pyridinyl)-2-propenoic acid or an addition salt with a pharmaceutically-acceptable acid or base.

11. A compound of claim 1, which is selected from (E)-3-[5,6-bis(benzyloxy)-3-(3-pyridinyloxy)benzo[b]thiophen-2-yl]-2-(4-pyridinyl)-2-propenoic acid or an addition salt with a pharmaceutically-acceptable acid or base.

12. A compound of claim 1, which is selected from (E)-3-[5,6-bis(benzyloxy)-3-(4-hydroxyphenoxy)benzo[b]thiophen-2-yl]-2-(4-pyridinyl)-2-propenoic acid or an addition salt with a pharmaceutically-acceptable acid or base.

13. A compound of claim 1, which is selected from (E)-3-{5,6-bis(benzyloxy)-3-[(6-methyl-3-pyridinyl)oxy]benzo[b]thiophen-2-yl}-2-(4-pyridinyl)-2-propenoic acid or an addition salt with a pharmaceutically-acceptable acid or base.

14. A compound of claim 1, which is selected from (E)-3-{5-(benzyloxy)-3-[4-(benzyloxy)phenoxy]-6-methoxy-benzo[b]thiophen-2-yl}-2-(4-pyridinyl)-2-propenoic acid or an addition salt with a pharmaceutically-acceptable acid or base.

15. A compound of claim 1, which is selected from (E)-3-[5,6-bis(benzyloxy)-3-(6-quinolinyloxy)benzo[b]thiophen-2-yl]-2-(4-pyridinyl)-2-propenoic acid or an addition salt with a pharmaceutically-acceptable acid or base.

16. A compound of claim 1, which is selected from (E)-3-{5,6-bis(benzyloxy)-3-[(6-methoxy-3-pyridinyl)oxy]benzo[b]thiophen-2-yl}-2-(4-pyridinyl)-2-propenoic acid or an addition salt with a pharmaceutically-acceptable acid or base.

17. A compound of claim 1, which is selected from (E)-3-{5,6-bis(benzyloxy)-3-[4-(4-pyridinyl)phenoxy]-benzo[b]thiophen-2-yl }-2-(4-pyridinyl)-2-propenoic acid or an addition salt with a pharmaceutically-acceptable acid or base.

18. A compound of claim 1, which is selected from (E)-3-[5-benzyloxy-6-methoxy-3-(3-pyridinyl)oxy-benzo[b]thiophen-2-yl]-2-(4-pyridinyl)-2-propenoic acid or an addition salt with a pharmaceutically-acceptable acid or base.

19. A pharmaceutical composition useful in the alleviation of thrombosis comprising as active principle an effective amount of a compound as claimed in claim 1, in combination with one or more pharmaceutically-acceptable excipients or carriers.

20. A method for effecting fibrinolysis in a living body in need thereof, comprising the step of administering to the living body an amount of a compound of claim 1, which is effective as an inhibitor of PAI-1.

\* \* \* \* \*

UNITED STATES PATENT AND TRADEMARK OFFICE
CERTIFICATE OF CORRECTION

PATENT NO. : 6,048,875
DATED : April 11, 2000
INVENTOR(S) : G.de Nanteuil, C. Lila, T. Verbeuren, A. Rupin It is certified that error appears in the above-identified patent and that said Letters Patent is hereby corrected as shown below:

Title Page,
Item [75] Inventors: "Manteuil" should read -- Nanteuil --.

Item [57] ABSTRACT:
Line 6: "or may a" should read: -- or may represent a--.

Column 5,
Line 28: "-2-4-pyridyl) -" should read -- -2-4-pyridinyl)- --.

Column 21,
Line 31: "Example 9" should read: -- Example 19 --.

Column 33,
Line 43 (approx): "-2H-15-" should read -- -2H-1,5- --.

Column 35,
Line 12: "($SO_2$ moiety" should read: -- (the $SO_2$ moiety --.
Line 17: Delete "the" at the end of the line.
Line 18: Insert -- the -- before "alkoxy".
Line 42: Insert --group of -- between "a" and "formula".

Column 36,
Line 15: Insert -- the -- before "alkoxy".
Line 15: Delete "the" before "alkyl moieties".
Line 57: Insert --a -- after the word "or".

UNITED STATES PATENT AND TRADEMARK OFFICE
CERTIFICATE OF CORRECTION

PATENT NO.   : 6,048,875
DATED        : April 11, 2000
INVENTOR(S)  : G.de Nanteuil, C. Lila, T. Verbeuren, A. Rupin It is certified that error appears in the above-identified patent and that said Letters Patent is hereby corrected as shown below:

Column 37,
Line 18: After "claim 1," insert the word -- wherein: --.

Signed and Sealed this

Third Day of July, 2001

*Attest:*

*Attesting Officer*

NICHOLAS P. GODICI
*Acting Director of the United States Patent and Trademark Office*